(12) United States Patent
Stevenson et al.

(10) Patent No.: US 8,248,232 B2
(45) Date of Patent: *Aug. 21, 2012

(54) HERMETICALLY SEALED RFID MICROELECTRONIC CHIP CONNECTED TO A BIOCOMPATIBLE RFID ANTENNA

(75) Inventors: Robert A. Stevenson, Canyon Country, CA (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 323 days.

This patent is subject to a terminal disclaimer.

(21) Appl. No.: 12/728,538

(22) Filed: Mar. 22, 2010

(65) Prior Publication Data

US 2010/0194541 A1 Aug. 5, 2010

Related U.S. Application Data

(63) Continuation-in-part of application No. 12/566,223, filed on Sep. 24, 2009, which is a continuation-in-part of application No. 11/307,145, filed on Jan. 25, 2006, now Pat. No. 7,916,013.

(51) Int. Cl.
*G08B 1/08* (2006.01)
*G08B 23/00* (2006.01)
*A61B 5/00* (2006.01)
*H01Q 1/00* (2006.01)

(52) U.S. Cl. ............. 340/539.12; 340/572.1; 340/573.1; 600/300; 600/301; 128/903; 343/720; 343/873

(58) Field of Classification Search ............. 340/539.12, 340/572.1
See application file for complete search history.

(56) References Cited

U.S. PATENT DOCUMENTS

| 4,376,441 | A | 3/1983 | Duncan |
| 4,424,551 | A | 1/1984 | Stevenson et al. |
| 4,846,158 | A | 7/1989 | Teranishi |
| 5,333,095 | A | 7/1994 | Stevenson et al. |
| 5,336,158 | A | 8/1994 | Huggins et al. |
| 5,342,408 | A | 8/1994 | deCoriolis et al. |
| 5,855,609 | A | 1/1999 | Knapp |
| 5,905,627 | A | 5/1999 | Brendel et al. |
| 5,963,132 | A | 10/1999 | Yoakum |
| 6,216,038 | B1 | 4/2001 | Hartlaub et al. |
| 6,259,937 | B1 | 7/2001 | Schulman et al. |
| 6,275,369 | B1 | 8/2001 | Stevenson et al. |
| 6,342,839 | B1 | 1/2002 | Curkendall et al. |

(Continued)

FOREIGN PATENT DOCUMENTS

EP 0 534 782 A1 3/1983

(Continued)

OTHER PUBLICATIONS

U.S. Appl. No. 60/478,717, filed Jun. 16, 2003, Off.

(Continued)

*Primary Examiner* — Donnie Crosland
(74) *Attorney, Agent, or Firm* — Michael F. Scalise

(57) ABSTRACT

An implantable radio frequency identification (RFID) tag includes a hermetically sealed biocompatible housing for an active implantable medical device (AIMD), an RFID microelectronics chip is disposed within the housing, and a biocompatible antenna extends from the RFID microelectronic chip and exteriorly of the housing. In a preferred form of the invention, the antenna is disposed within a header block of the AIMD, and the RFID chip is disposed within the AIMD housing.

41 Claims, 14 Drawing Sheets

U.S. PATENT DOCUMENTS

| | | | |
|---|---|---|---|
| 6,375,780 | B1 | 4/2002 | Tuttle et al. |
| 6,566,978 | B2 | 5/2003 | Stevenson et al. |
| 6,735,479 | B2 | 5/2004 | Fabian et al. |
| 6,765,779 | B2 | 7/2004 | Stevenson et al. |
| 6,957,107 | B2 | 10/2005 | Rogers et al. |
| 7,017,822 | B2 | 3/2006 | Aisenbrey |
| 7,103,413 | B2 | 9/2006 | Swanson et al. |
| 7,174,201 | B2 | 2/2007 | Govari et al. |
| 7,240,833 | B2 | 7/2007 | Zarembo |
| 7,256,695 | B2 | 8/2007 | Hamel et al. |
| 7,333,013 | B2 | 2/2008 | Berger |
| 7,479,108 | B2 | 1/2009 | Rini et al. |
| 7,916,013 | B2 * | 3/2011 | Stevenson ................ 340/539.12 |
| 2002/0151770 | A1 | 10/2002 | Noll et al. |
| 2003/0181794 | A1 | 9/2003 | Rini et al. |
| 2008/0048855 | A1 | 2/2008 | Berger |
| 2008/0065181 | A1 | 3/2008 | Stevenson |

FOREIGN PATENT DOCUMENTS

| | | |
|---|---|---|
| EP | 0 619 101 A1 | 10/1994 |
| WO | WO 96/11722 A1 | 4/1996 |

OTHER PUBLICATIONS

Wesley J. Clement and Bob Stevenson; Lead Loop Area Measurement of Implantable Pulse Generations and Cardioverter/Defibrillators for Determination of Susceptibility to Radiated Electromagnetic Interference; Heart Rhythm 2005; May 5, 2005; Abstract: 05-AB-2928-HRS, New Orleans, LA.

* cited by examiner

HERMETICALLY SEALED RFID MICROELECTRONIC CHIP CONNECTED TO A BIOCOMPATIBLE RFID ANTENNA

CROSS-REFERENCE TO RELATED APPLICATIONS

The present application is a continuation-in-part of application Ser. No. 12/566,223, filed on Sep. 24, 2009, which is a continuation-in-part of application Ser. No. 11/307,145, filed on Jan. 25, 2006 now U.S. Pat. No. 7,916,013.

BACKGROUND OF THE INVENTION

This invention relates generally to methods of identifying implanted medical devices. More specifically, this invention relates to implantable and biocompatible radio frequency identification (RFID) tags and associated antennas which may be used with medical devices or for general personal identification purposes.

There are known in the art various methods for identifying implanted medical devices. One such method is the use of X-ray identification tags encapsulated within header blocks of pacemakers or implantable cardioverter defibrillators (ICD). Such X-ray identification tags can be read on an X-ray of the implanted device and provide information to the physician. The information so provided is limited due to space and typically includes only the manufacturer and model number of the implanted device.

It would be beneficial if physicians were able to obtain additional information about an implanted device and/or a patient from an implanted identification tag. Such beneficial information includes, in addition to the manufacturer and model number of the device, the serial number of the device, the treating physician's name and contact information and, if authorized by the patient, the patient's name, contact information, medical condition and treatment, and other relevant information.

Currently, most active implantable medical device (AIMD) patients carry some sort of identification. This could be in the form of a card carried in the wallet or an ID bracelet indicating, for example, that they are a pacemaker wearer of a certain model and serial number. However, such forms of identification are often not reliable. It is quite common for an elderly patient to be presented at the emergency room (ER) of a hospital without their wallet and without wearing any type of a bracelet. In addition, there have been a number of situations where the patient (due to dementia or Alzheimer's, etc.) cannot clearly state that he or she even has a pacemaker.

Oftentimes the ER physician will palpitate the patient's chest and feel that there is an implanted device present. If the patient is comatose, has low blood pressure, or is in another form of cardiac distress, this presents a serious dilemma for the ER. At this moment in time, all that the ER knows is that the patient has some sort of an AIMD implant in his or her chest. It could be a pacemaker, a cardioverter defibrillator, or even a vagus nerve stimulator or deep brain stimulator.

What happens next is both laborious and time consuming. The ER physician will have various manufacturers' internal programmers transported from the hospital cardiology laboratory down to the ER. ER personnel will then try to interrogate the implantable medical device to see if they can determine what it is. For example, they might first try to use a Medtronic programmer to see if it is a Medtronic pacemaker. Then they might try a St. Jude, a Guidant, an ELA, a Biotronik or one of a number of other programmers that are present. If none of those programmers work, then the ER physician has to consider that it may be a neurostimulator and perhaps go get a Cyberonics or Neuropace programmer.

It would be a great advantage and potentially lifesaving if the ER physician could very quickly identify the type of implant and model number. In certain cases, for example, with a pacemaker patient who is in cardiac distress, with an external programmer they could boost the pacemaker output voltage to properly recapture the heart, obtain a regular sinus rhythm and stabilize blood pressure. All of the lost time running around to find the right programmer, however, generally precludes this. Accordingly, there is a need for a way to rapidly identify the type and model number of an active implantable medical device so that the proper external programmer for it can be rapidly identified and obtained.

It is also important to note that lead wire systems generally remain in the human body much longer than the active implantable medical device itself. For example, in the case of a cardiac pacemaker, the cardiac pacemaker batteries tend to last for 5 to 7 years. It is a very difficult surgical procedure to actually remove leads from the heart once they are implanted. This is because the distal TIP and other areas of the leads tend to become embedded and overgrown (encapsulated) by tissues. It often takes very complex surgical procedures, including lasers or even open heart surgery, to remove such lead wire systems. When a pacemaker is replaced, the pectoral pocket is simply reopened and a new pacemaker is plugged into the existing leads. However, it is also quite common for leads to fail for various reasons. They could fail due to breakdown of electrical insulation or they could migrate to an improper position within the heart. In this case, the physician normally snips the leads off and abandons them and then installs new leads in parallel with the old abandoned leads.

Abandoned leads can be quite a problem during certain medical diagnostic procedures, such as MRI. It has been demonstrated in the literature that such leads can greatly overheat due to the powerful magnetic fields induced during MRI. Accordingly, it is important that there be a way of identifying abandoned leads and the lead type. Also, there is a need to identify such abandoned leads to an Emergency Room physician or other medical practitioner who may contemplate performing a medical diagnostic procedure on the patient such as MRI. This is in addition to the need to also identify the make and model number of the active implantable medical device.

It is also important to note that certain lead systems are evolving to be compatible with a specific type of medical diagnostic procedure. For example, MRI systems vary in static field strength from 0.5 Tesla all the way above 10 Tesla. A very popular MRI system, for example, operates at 3 Tesla and has a pulse RF frequency of 128 MHz. There are specific certain lead systems that are evolving in the marketplace that would be compatible with only this type of MRI system. In other words, it would be dangerous for a patient with a lead wire designed for 3 Tesla to be exposed to a 1.5 Tesla system. Thus, there is also a need to identify such lead systems to Emergency Room and other medical personnel when necessary. For example, a patient that has a lead system that has been specifically designed for use with a 3 Tesla MRI system may have several pacemaker replacements over the years.

It is already well known in the prior art that RFID tag implants can be used for animals, for example, for pet tracking. They are also used in the livestock industry. For example, RFID tags can be placed in or on cattle to identify them and track certain information. An injectable RFID tag for humans has also been developed. However, none of the current RFID tags have been designed to have long term reliability, hermeticity, and biocompatibility within the body fluid environment.

In the prior art, RFID tags have been encapsulated in plastic or placed in a plastic or glass tube with an epoxy infill. However, as will be discussed more fully below, none of these materials provide a truly hermetic seal against body fluids.

With reference now to FIGS. 1 and 2, prior art RFID tags 12 typically involve a small substrate 14 on which a microelectronic chip 16 is placed along with an embedded or printed antenna 18. These antennas can be Wheeler spirals, rectangles, dipoles, solenoids or other shapes. The read range of such antennas, particularly for low frequency (LF) and high frequency (HF) readers tends to be very short. That is, the RFID reader has to be in very close proximity to the RFID chip. In order to extend the read range, a larger loop style antenna 18 involving multiple turns, as illustrated in FIG. 2, is typically used. These involve very fine wire, multiple turns of copper, which are then soldered to the RFID chip. Obviously, neither copper nor solder joints are biocompatible or even reliable for human body implants. When exposed to body fluids, copper causes corrosion problems as well the tin and lead that is typically used in solders. These materials, when leached out can even become toxic to the human body.

One approach would be to hermetically seal the RFID chip and its complete loop antenna. However, when one fully contemplates hermetically sealing an RFID chip with a very large multi-turn loop antenna, one realizes that such an approach becomes entirely impractical. The hermetic seal package would simply be too large to be effectively associated with a medical implant.

Accordingly, there is a need for an improved medical identification tag that can store additional information about an implanted device and/or a patient, without unduly increasing the size of the identification tag or jeopardizing the operation of the implanted device or the health of the patient. The present invention meets these needs by providing an RFID tag whose electronic chip is enclosed within an AIMD hermetic housing, and a biocompatible antenna that is disposed outside of the AIMD housing. The RFID tag of the present invention is capable of storing information about the medical device, the physician, and the patient, as described above.

SUMMARY OF THE INVENTION

In general, the present invention is directed to a system for identifying implants within a patient, comprising an implantable medical device, a radio frequency identification (RFID) tag having a hermetically sealed chip and biocompatible antenna and being associated with the implantable medical device, the RFID tag containing information relating to the patient and/or the implantable medical device, and an interrogator capable of communicating with the RFID tag.

Such implantable medical devices may include active implantable medical devices (AIMD) such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion, or a prosthetic device and component parts thereof, including lead wires or abandoned lead wires.

More particularly, the present invention relates to an implantable radio frequency identification (RFID) tag, comprising: (1) a hermetically sealed biocompatible housing for an active implantable medical device (AIMD); (2) an RFID microelectronics chip disposed within the housing; and (3) a biocompatible antenna extending from the RFID microelectronics chip and exteriorly of the housing. The antenna may be disposed within a non-hermetically sealed portion of the AIMD, such as the AIMD header block.

With the biocompatible antenna disposed within the AIMD header block, at least one lead extends through a hermetic terminal associated with the AIMD housing to connect the antenna to the RFID tip which is disposed within the AIMD housing. The RFID chip may be disposed either adjacent to the hermetic terminal or remotely within the housing relative to the hermetic terminal. Moreover, at least one lead may comprise a unitary extension of the antenna and/or an active lead which extends through the hermetic terminal in non-conductive relation with the AIMD housing, and a ground lead extending through the AIMD housing in conductive relation.

The AIMD housing preferably has a leak rate of no more than $10^{-7}$ cubic centimeters per second. Preferably, the housing is taken from the group including biocompatible metals and alloys such as titanium and/or stainless steel, ceramic, glass, porcelain, sapphire and composites thereof, and specialty polymer composites, where the housing is of a non-conductive material, such as ceramic, glass or the like, then a metal coating would typically be used to provide an overall electromagnetic shield. A desiccant may further be disposed within the housing.

The RFID chip may be read-only or readable/writable, and may comprise a portion of a system which includes an interrogator for electromagnetically communicating with the RFID chip. The interrogator may be a read-only or a reader/writer device and, in turn, may be placed in communication with a computer or a computer network.

The RFID chip may include information pertaining to the AIMD and/or to a patient in which the RFID tag is implanted.

The antenna may be wound around a ferrite-based core comprising a high temperature sintered ferrite-based material having a biocompatible dielectric material at least partially coating the ferrite-based material. Such biocompatible dielectric material may comprise parylene, ETFE, PTFE, polyimide, polyurethane, or silicone. Preferably, the ferrite-based core is comprised of a ferrite material that will not exhibit permanent remanence after exposure to MRI fields.

A sensor may be conductively coupled to the RFID microelectronics chip. The sensor may be disposed either exteriorly of the AIMD housing or within the AIMD housing. The sensor may measure and the RFID tag may transmit measured properties in real time.

The RFID tag's biocompatible antenna may comprise at least one biocompatible conductive material taken from the group of: titanium, platinum and platinum/iridium alloys, tantalum, niobium, zirconium, hafnium, nitinol, Co—Cr—Ni alloys such as MP35N, Havar®, Elgiloy®, stainless steel, gold and its various alloys, palladium, pyrolytic carbon, or any other noble metal.

The RFID tag's biocompatible antenna may also comprise a conductive metal compound taken from any of the following: ZrC, ZrN, TiN, NbO, TiC and TaC, or a substrate and a conductive polymer taken from the group of: Polyethylene, oxide with ionic addition such as NaCl, Polyurethane, Silicone, Polyesters, Polycarbonate, polyethylene, Polyvinyl Chloride, Polypropylene, Methylacrylate, or Para-xylylene.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention is directed to a radio frequency identification (RFID) system for use with active implantable medical devices (AIMDs) and an associated RFID tag. Specifically, the RFID system comprises an RFID tag implanted in a patient's body and associated with an implanted AIMD, and an interrogator in communication with the RFID tag. The novel tag comprises an electronic RFID chip disposed inside the hermetically sealed housing of an AIMD, and an external biocompatible antenna.

Figure 1:
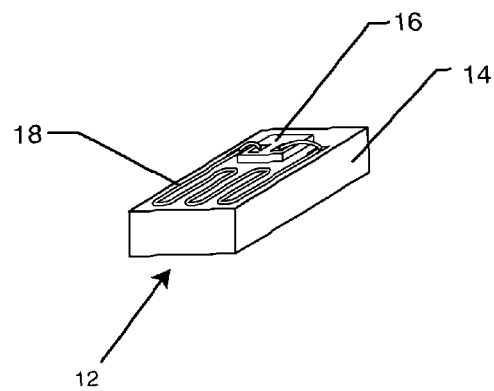
FIG. 1 is an isometric view of a prior art RFID tag.
Figure 2:
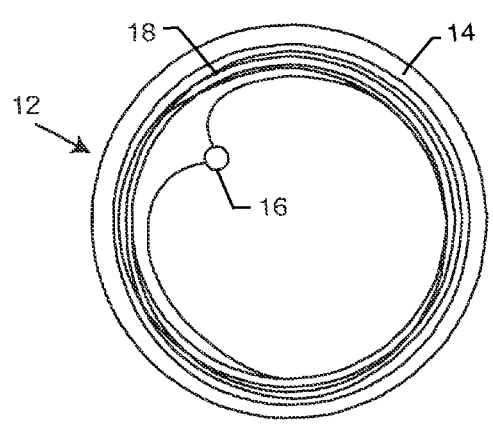
FIG. 2 illustrates a prior art RFID chip and associated antenna.
Figure 3:
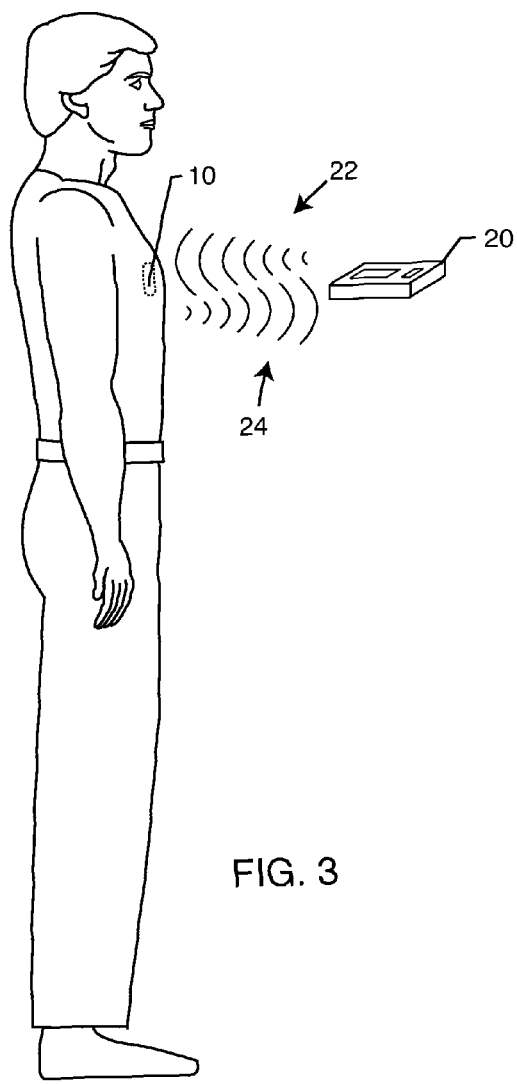
FIG. 3 is a depiction of a patient with an AIMD fitted with an RFID tag of the present invention and an external interrogator/reader.

FIG. 3 is an outline drawing of an adult male pacemaker patient with an AIMD 10. The location for the AIMD 10, shown by a dashed ellipse, is typical of a right or left pectoral muscle implant. Right and left pectoral muscle implants are typical for a cardiac pacemaker or implantable cardioverter defibrillator (ICD). The right and left pectoral muscle region is chosen due to the easy access to the cephalic or subclavian veins for transvenous insertion of lead wires and electrodes down into the heart. The present invention may also find application in human and other animal AIMDs such as an implantable defibrillator, a congestive heart failure device, a hearing implant, a cochlear implant, a neurostimulator, a drug pump, a ventricular assist device, a drug pump, a spinal cord stimulator, an implantable sensing system, a deep brain stimulator, an artificial heart, an incontinence device, a vagus nerve stimulator, a bone growth stimulator, a gastric pacemaker, or a prosthetic device.

An RFID interrogator 20, also known as a hand held scanner or reader, transmits an electromagnetic field pulse 22 which is intercepted by the antenna 18 that is part of the implanted RFID tag 12. The implanted RFID tag 12 is generally passive, which means that it does not have its own self-contained source of energy such as a battery (although it can). The electromagnetic field pulse 22 that comes from the interrogator 20 resonates with the antenna 18 and the RFID chip 16 providing energy for the RFID chip 16 to generate a signal and the antenna 18 to emit a return pulse 24. There is usually an energy storage and resonant capacitor 158 (FIGS. 21-23) that is in parallel with the RFID electronic chip 16 and the antenna 14. This capacitor resonates with the antenna and also stores energy sufficient to power the passive RFID chip 16. The return pulse 24 is picked up by an antenna 26 (FIG. 4) in the interrogator 20. The return pulse 24 can be digitally modulated to contain information such as the model number of the patient's AIMD, the serial number of the AIMD, the manufacturer of the lead wire system, the name of the patient's physician, and contact information for the physician. In addition, if the patient authorizes, the digital pulses can also contain the patient's name, the patient's medical condition, the patient's address and telephone number, and other pertinent information.

Figure 4:
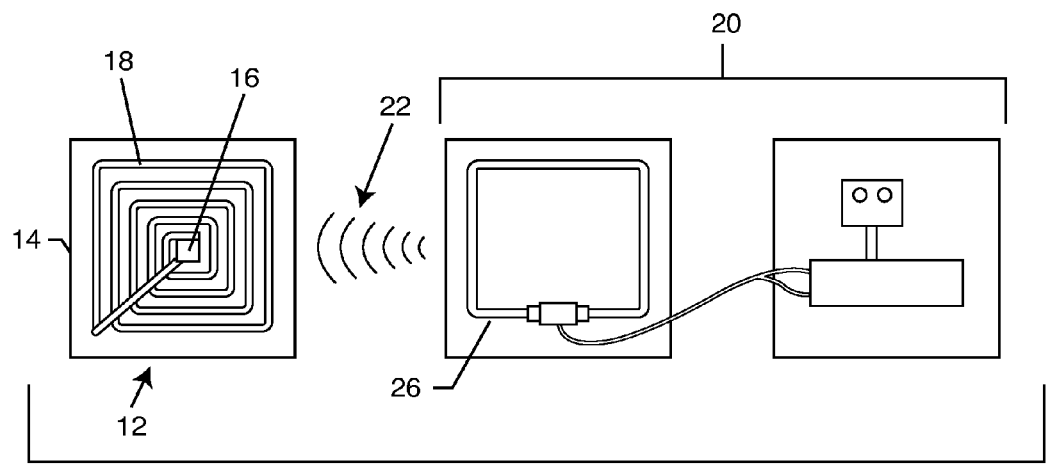
FIG. 4 is a block diagram depicting operation of a system including the RFID tag of the present invention.
Figure 5:
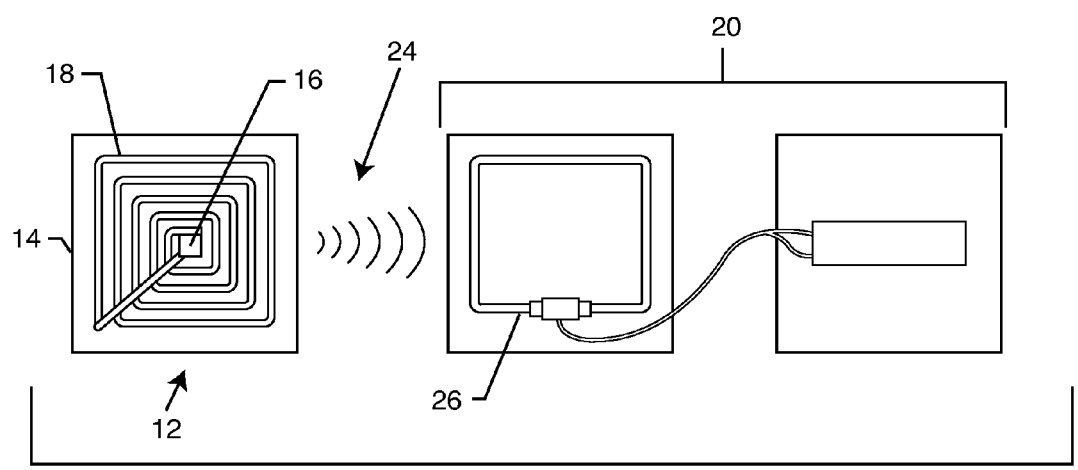
FIG. 5 is a block diagram depicting operations of an alternative system including an RFID tag.

FIGS. 4 and 5 depict block diagrams of the RFID system in operation. As described above, the RFID tag 12 consists of a substrate 14, an RFID chip 16, and an antenna 18. The interrogator 20 with associated antenna 26, discharges an electromagnetic energy pulse 22 to the antenna 18 of the RFID tag 12, which powers up the RFID chip 16 and allows it to produce the electromagnetic return pulse signal 24, as shown. The electromagnetic return signal 24 is detected by the interrogator 20 and presented as a digital code sequence. The RFID tag 12 may be read-only (RO) or read/write (RW). With an RW RFID tag 12, a physician may use an external programmer or interrogator 20 to write additional patient information to the RFID tag 12. This additional information may include patient name, patient address, medical condition, and so on. In the case of an RO RFID tag 12, the RFID tag 12 would be installed at the time of AIMD manufacture and would include manufacturer, model number and other key information. However, an RO RFID tag 12 would not be later programmable and could not include added important information such as patient name, doctor name, patient diagnosis and so forth. The interrogator 20 may comprise programmer or programmer/reader, which would permit direct display of all of the information contained on the RFID tag 12.

Ideally, the medical device manufacturer would have a special RFID reader associated with their manufacturing line. For example, a cardiac pacemaker manufacturer, at the point of final sterilization and packaging, would use a production line barcode reader-RFID writer to read a barcode associated with the production lot traveler or packaging, and then the production line RFID writer would write this information to the RFID tag that is embedded in or associated with the pacemaker or other medical device. This would go into an area of permanent memory on the RFID tag. There would also be an area of volatile memory that the doctor could optionally use later to enter information about the patient, the patient's medical condition or even information about the implanting physician all at the time of implant. This would typically be done with informed patient consent. Of course, these principles are applicable to any external or internal medical device.

Figure 6:
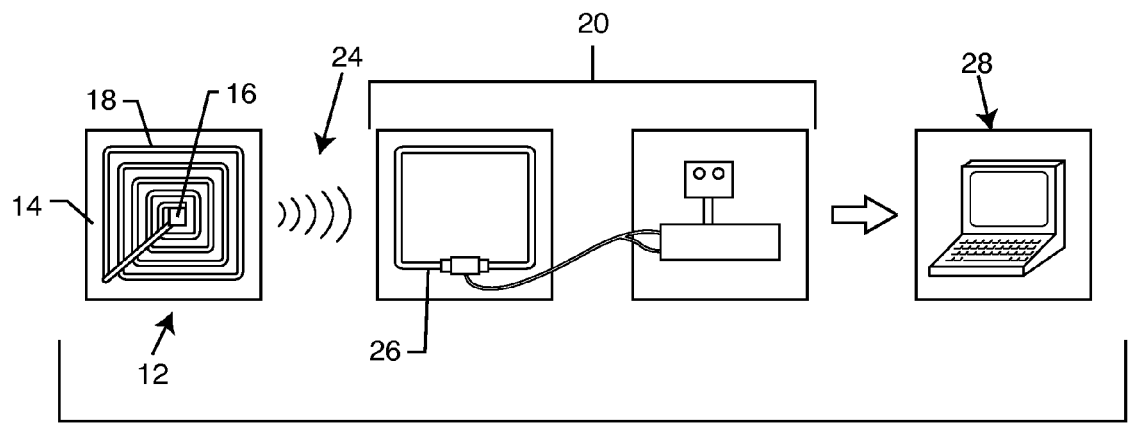
FIG. 6 is a block diagram depicting operation of another alternative system including an RFID tag.

FIG. 6 illustrates a very similar system as previously described in FIGS. 4 and 5 except that the interrogator 20 is designed to be integrated with a computer system 28 which may be linked to the worldwide web. In this case, a unique digital number transmitted by the RFID tag 12 may be entered into the computer system 28. The computer system 28 maintains a database of important information that is all keyed to the digital information transmitted by the RFID tag 12. In this way, the physician or emergency room personnel may obtain the digital code from the RFID tag 12 which enters automatically (or manually) into the computer system 28 to immediately get a download, including all of the information required as to the model and serial number of the AIMD, lead wire system, patient and physician information, and patient history when available. The RFID tag 12 could also access the new American College of Cardiology National Cardiovascular Data Registry (ACC-NCDR). ACC-NCDR is a comprehensive cardiac and date repository for three national registries: the CathPCI Registry, the Carotids tent Registry, and the ICD Registry. The ICD Registry was developed in partnership with the Heart Rhythm Society and is designed for participation by hospitals. It collects detailed information on ICD implantations and has as one of its missions helping hospitals meet regulatory requirements and Medicare requirements.

Figure 7:
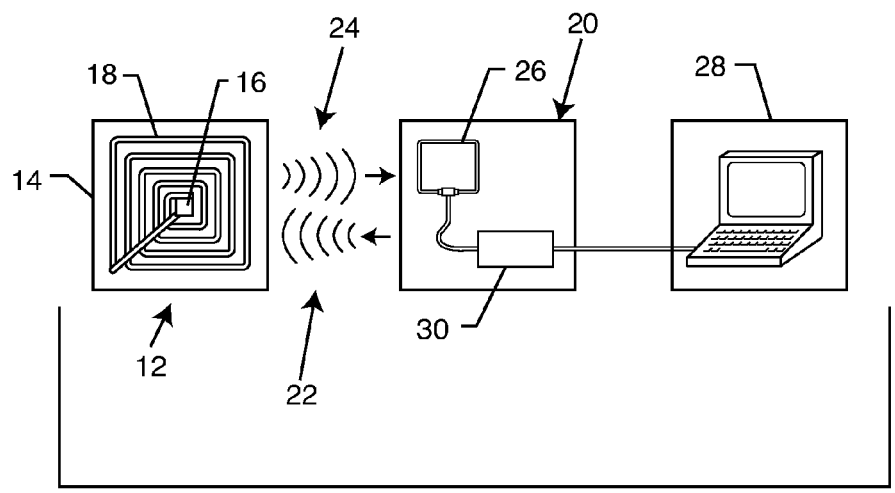
FIG. 7 is a block diagram depicting operation of yet another alternative system including an RFID tag of the present invention.

FIG. 7 illustrates a system very similar to that shown in FIG. 6 except that the output of the interrogator 20 would go to an antenna and processor 30 which are designed to be linked directly to a laptop computer 28 or a local area network (LAN) or a wide area network (WAN). This could be done by USB or equivalent cable interface network. The laptop computer 28 may contain a full database by model numbers and serial numbers of medical implantable devices. A drawback to this type of system is that it would be very difficult to keep updated with current patient and physician information.

RFID standards are evolving worldwide at various frequencies generally between 125 kHz and 915 MHz. For example, a 915 MHz protocol is generally evolving to be used for retail goods and inventory control. However, due to the high frequency, the 915 MHz protocols are not very useful for human implants. The reason for this is that humans are largely water and 915 MHz fields are greatly affected by the presence of water. The preferred embodiment is another RFID protocol which operates at 13.56 MHz which is ideal for an implantable RFID tag. The 13.56 MHz lower frequency will readily penetrate and communicate with the tag instead of reflecting off of the skin surface or being absorbed. There are other lower frequency RFID systems, for example, in the 50 to 135 kHz range which would also be ideal.

Figure 8:
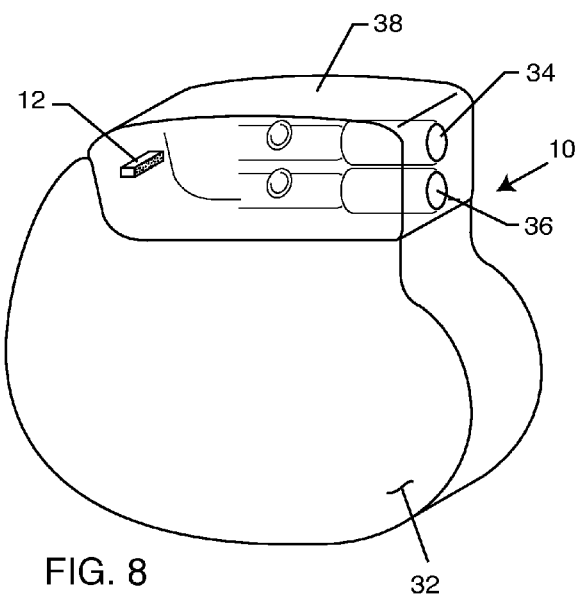
FIG. 8 is an isometric view of a typical AIMD fitted with an enclosed RFID tag.

FIG. 8 is an isometric view of a AIMD 10, such as a cardiac pacemaker. Cardiac pacemakers typically have a metallic housing 32 which can be of titanium, stainless steel or the like. This metallic housing 32 is laser welded shut and generally contains a hermetic feedthrough terminal for passage of lead wires into the interior of the metallic housing 32. Said hermetic feedthrough terminals are well known in the art and are generally laser welded into the metallic housing 32 of the AIMD. The cardiac leads (not shown) are generally routed to ISO IS-1 connectors 34, 36. The connectors 34, 36 provide a convenient location to plug in the leads which are routed to the heart for pacing and biologic sensing. The connectors 34 and 36 are generally encapsulated within a molded, non-metallic, i.e., plastic (such as Techothane) or ceramic, header block 38. Usually, this header block 38 is of clear casting materials which are well known in the art. Opaque thermal setting or chemically setting materials may also be used.

A non-hermetically sealed RFID tag 12 is encapsulated within the molded header block 38 of the AIMD 10. Such molded header connector blocks are common in the industry and are designated by ISO Standards IS-1, DF-1 or IS-4 or the equivalent. The header block 38 of FIG. 8 is formed of a solid encapsulated material such as an epoxy, thermal setting polymer like Techothane, or the like. In general such materials are not considered truly hermetic and will have leak rates varying from $10^{-3}$ to $10^{-5}$ cubic centimeters per second. Accordingly, if the AIMD 10 of FIG. 8 were implanted for long periods of time, then body fluids would eventually reach the electronic circuits (microchip 16) of the RFID tag 12 due to the bulk permeability of the header block 38 material. Body fluids are comprised primarily of water and dissolved salts including sodium, chlorine, potassium, calcium and the like. These are ionic and if they reach the surfaces of the RFID tag microchip 16 it will readily short it out. Worse still, the RFID tag 12 itself may contain materials that are not biocompatible and may be toxic to body tissues. For example, when the RFID microchip 16 is viewed under high magnification, one can see that there are hundreds, if not thousands of non-biocompatible electronic circuit connections, which can contain tin, cadmium or even lead.

Prior art RFID tags (like the Verichip) that are used for both animal and sometimes for human implant have a serious deficiency in that they are not truly hermetically sealed. These devices often use a cylindrical glass cup which is filled with epoxy or other types of polymer materials such as silicone or the like. A deficiency with such seals is that over long periods of time moisture will slowly penetrate and reach the sensitive electronic circuits. When moisture reaches electronic circuits under low bias voltage conditions, dendrites and tin whiskers can form thereby shorting out or reducing insulation resistancy to electronic components. Accordingly, the RFID chip should be completely hermetically sealed in a container with a minimum helium leak rate of $1\times10^{-7}$ cubic centimeters per second. As used herein "hermetically sealed" means a leak rate of $10^{-7}$ cubic centimeters per second or slower. This is in sharp contrast to prior art polymer fill systems which achieve at most a helium leak rate of around $1\times10^{-5}$ cubic centimeters per second. In the most preferred embodiment described herein, the electronic chip portion of the RFID tag 12 is hermetically sealed inside the overall housing of the AIMD.

Since the RFID chip 16 is generally constructed of materials that are not long-term biocompatible and body fluid resistant, it is important to prevent body fluids from reaching the RFID chip 16. Even if the RFID chip 16 is embedded deeply within a molded polymer header block 38 as illustrated in FIG. 8, when such a device is implanted into body tissue for many years (cochlear implants may last forty years or longer), moisture can slowly penetrate due to the bulk permeability of the polymer material of the header block 38. In the art, this is known as the leak rate or hermeticity of a device. Generally speaking, adjunct sealants, polymers and the like are not considered truly hermetic. A helium leak rate of $10^{-7}$ cubic centimeters per second or slower is required to assure that moisture will not penetrate to sensitive electronics over long periods of time. In order to achieve such low leak rates, generally glass seals or gold brazed ceramic seals are required. It is well known that brazed ceramic seals are generally superior to fused or compression glass seals.

In order for the RFID interrogator 20 to be able to read a tag 12 embedded within the human body, it must generate a very powerful yet relatively low frequency field. Such interrogators 20 are most effective when held within ten centimeters of the implant.

Figure 9:
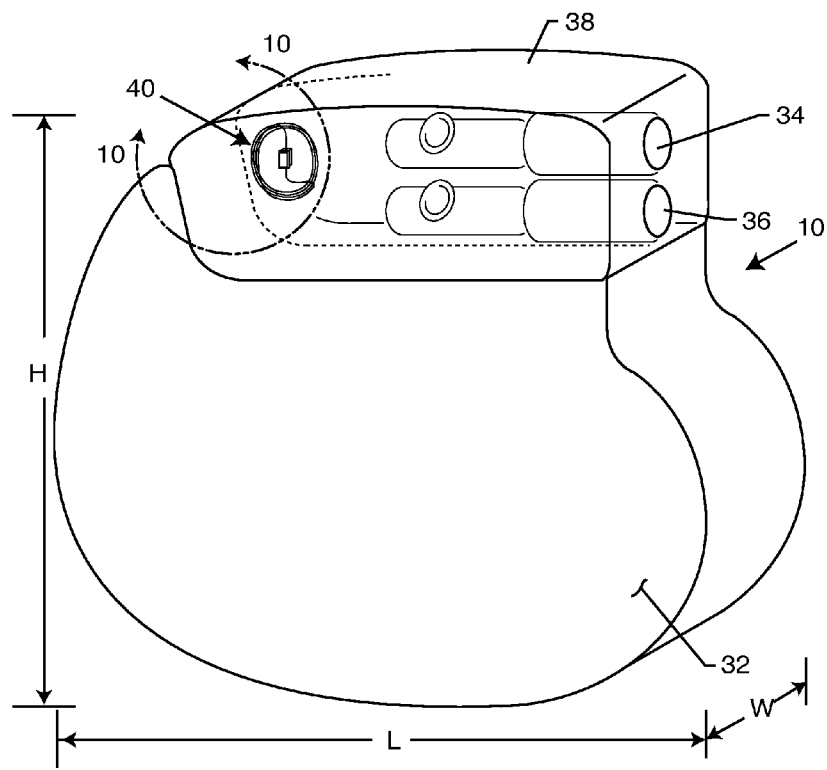
FIG. 9 is an isometric view of a typical AIMD similar to FIG. 8 fitted with an RFID tag disposed within a hermetic enclosure, wherein a biocompatible loop antenna extends outwardly from the hermetic container.

FIG. 9 is very similar to FIG. 8, except that an RFID tag 40 in one preferred form of the present invention is shown embedded within the plastic header block 38. The reason one would place the RFID tag 40 in the header block 38 is that the header block materials are non-metallic and are therefore transparent to electromagnetic energy from an RFID reader. This is particularly advantageous if the RFID frequency were to be at 13.56 MHz or above. For low frequency RFID tags (LF) that operate typically at 50 to 135 kHz range, the RFID tag 40 could be in the header block 38 or even inside the titanium housing 32 of the AIMD 10. However, to achieve optimum read range, it's preferable that the RFID tag's antenna 42 not be inside the electromagnetic shielded housing 32 of the AIMD 10.

Figure 10:
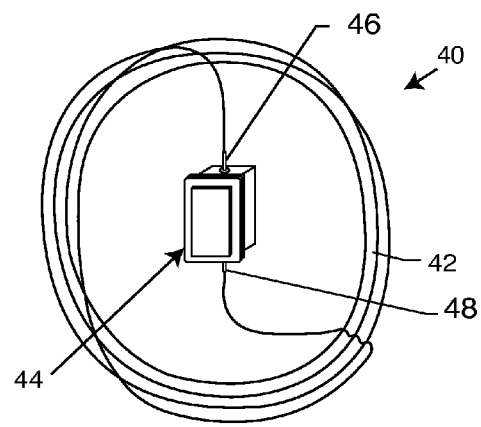
FIG. 10 is an enlarged view of an RFID tag taken of the area indicated by the line 10-10 in FIG. 9.

In FIGS. 9 and 10, the RFID tag 40 has been embedded in the header block 38 and is connected to a multiple-turn antenna 42. Read range is important in the present application. The read range should not be too excessive (for example, several meters) because of the possibility of creating electromagnetic interference (picking up stray tags and so on). However, a read range of approximately four to six inches would be optimal. Most implantable medical devices, such as cardiac pacemakers and implantable cardioverter defibrillators (ICDs) are implanted under the skin. In these cases, the implant depth would only be about 12 millimeters. However, for a person who is morbidly obese, this distance could increase significantly, especially if the implant was placed subpectorally or in a pocket down beneath the breast. In this case, a read range closer to 100 millimeters would be desirable. One might be tempted to place the RFID tag 40, closer to one side of the header block than the other. The problem with this is one cannot rely on the implanting physician to always implant the device with one side up. Furthermore, there is the syndrome that has been well documented in the art as Twiddler's Syndrome. Twiddler's Syndrome involves the pacemaker (or other AIMD) patient, either consciously or subconsciously, manipulating their implanted device. There have been documented cases that over a period of months or even years, the pacemakers have been twisted several times in the pocket to the point where the leads are broken or pulled out. Accordingly, the RFID circular antenna 42 would be implanted parallel to the length and height (L, H) plane of the AIMD 10 and midway or halfway in width W. In this case, it would not really matter which side was up when the physician implanted the device as the distance to the RFID antenna would remain constant. This also solves the issue with Twiddler's Syndrome in that it would not matter, again, which way the pacemaker was oriented.

FIG. 10 is an enlarged view of the RFID tag 40 of FIG. 9. The multiple turn loop antenna 42 consists of biocompatible conductive materials, such as titanium, platinum and platinum/iridium alloys, tantalum, niobium, zirconium, hafnium, nitinol, Co—Cr—Ni alloys such as MP35N, Havar®, Elgiloy®, stainless steel, gold and its various alloys, palladium, or any other biocompatible or noble metal. Conductive metal compounds could also be used to form a biocompatible antenna of the present invention and these include: ZrC, ZrN, TiN, NbO, TiC and TaC. In addition, the antenna 42 could be formed on some sort of a substrate with conductive polymers: Polyethylene Oxide with ionic addition such as NaCl (see U.S. Pat. No. 6,295,474), also, any of the commonly used implantable polymers, such as Polyurethane, Silicone, Polyesters, Polycarbonate, polyethylene, Polyvinyl Chloride, Polypropylene, Methylacrylate, Para-xylylene. These can all be made conductive by adding a biocompatible particulate filler, such as platinum powder or flake. Another type of conductive biocompatible material, from which the antenna 42 could be made, is pyrolytic carbon.

A hermetically sealed package 44 contains the RFID chip therein. There are biocompatible electrical connection terminal pins 46 and 48 between the antenna 42 and the hermetically sealed package 44. These would typically be laser welds or brazes of all biocompatible materials or biocompatible solders or conductive polymers. In other words, no non-biocompatible solder joint or other such non-biocompatible connection would be exposed to body fluids. An alternative would be to use a biocompatible thermally conductive adhesive. Biocompatible metals and alloys that can be used for the electronic network components or component network or the connection materials include all of the metals and alloys of titanium, platinum and platinum iridium alloys, tantalum, niobium, zirconium, Hafnium, nitinol, Co—Cr—Ni alloys such as MP35N, Havar®, Elgiloy®, stainless steel and gold. There are also a number of conductive metal compounds that can be used including ZrC, ZrN, TiN, NbO, TiC, TaC, and Indium Oxide/Indium Tin Oxide (Transparent Conductive Oxides). Commercially available biocompatible electrically conductive epoxies are manufactured by Epoxy Technology, Inc, in Billerica, Mass. For example Epoxy technology EPO-TEK H81 features a biocompatible epoxy which is gold filled (www.epotek.com). The conductive connection materials are typically thermal-setting, brazing, welding or special biocompatible soldering materials. So as to be non-migratable, these materials are selected from the group consisting of: gold, gold alloy, platinum, gold-filled-thermal-setting conductive material, platinum-filled-thermal-setting conductive material, gold-bearing glass frit, TiCuSil, CuSil, and gold-based braze.

Referring once again to FIG. 9, one can see that the RFID tag 40 satisfies all the needs for long term human implant. The header block 38 is not considered by biomedical scientists to be a long term or reliable hermetic seal. Over time, through bulk permeability, body fluids and water will penetrate readily through that entire structure. This is why the AIMD housing 32 is hermetically sealed to make sure that body fluids can never penetrate to the sensitive electronic circuits of the AIMD 10, as further explained by U.S. Patent Publication No. US 2006-0212096 A1, the contents of which are incorporated herein. The same principle applies in the present invention in that the sensitive microelectronic RFID chip 50 (FIG. 11) and its associated electrical connections must also be protected over the long term from body fluid intrusion.

Figure 11:
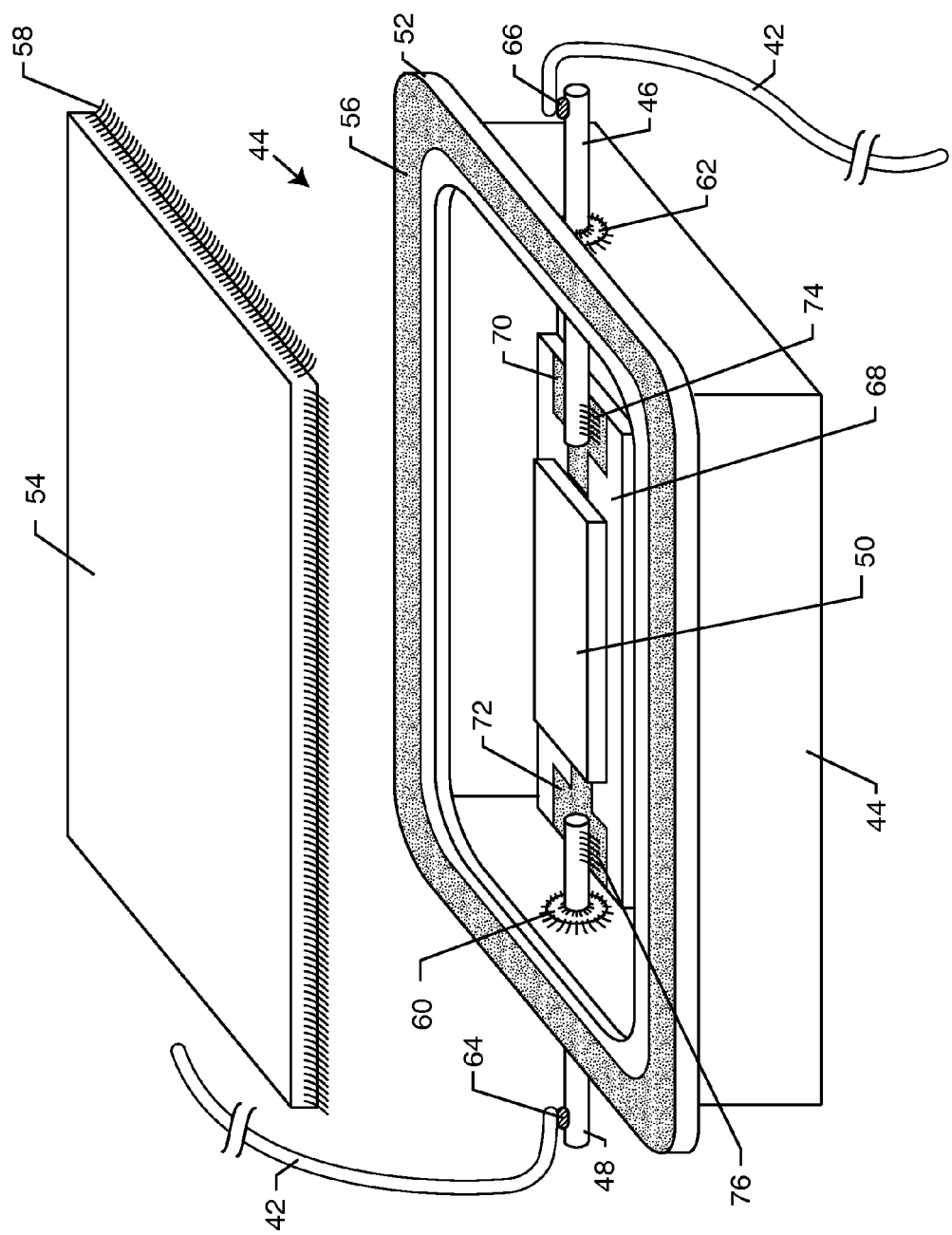
FIG. 11 is an exploded perspective view of the hermetic housing for the RFID chip illustrated in FIG. 10.

FIG. 11 shows the RFID chip 50 inside the hermetically sealed package 44. The package can be ceramic with a weld ring 52 and a ceramic lid 54 with a sputtered surface 56 as shown. The weld ring is typically titanium or platinum and is gold brazed 58 to the sputtered ceramic material 56. However, the entire package 44 can simply be machined or made from powder metallurgy of titanium so that the entire structure is metal. Through this would penetrate hermetic seals 60 and 62 on each end. These hermetic seals are preferably gold brazed ceramic seals, but they may also be either fusion or glass compression seals. The terminal pins 46 and 48 extend out either end for convenient welding of the antenna 42 lead at locations 64 and 66. This is typically done by laser welding so that it would be entirely biocompatible. As previously mentioned, this could also be done with a biocompatible thermal-setting conductive adhesive. The RFID chip 50 may be attached to the package 44 by means of a non-conductive substrate 68. Wire bond pads or metallizations 70 and 72 are formed on the substrate 68 to conductively couple the RFID chip 50 and the terminal pins 46 and 48, such as by gold braze or laser welds 74 and 76. Since these electrical connections 74 and 76 will not be exposed to body fluids, they may be comprised of solder or any other well-known non-biocompatible material.

Referring once again to FIG. 11, electrical connections (welds) 64 and 66 can be eliminated by using a suitable biocompatible antenna wire 42, such as platinum or platinum-iridium. One could take a setter, which would be typically of zirconia into which ceramic powder could be placed, which would roughly have the shape of housing 44. The antenna lead wire 42 could be of pure platinum or platinum-iridium, which is a high temperature material. The antenna could be laid through the powder in the same position as the pins 46 and 48 are presently shown. This entire structure could be co-fired (sintered) such that the platinum antenna lead forms its own hermetic seal into the hermetically sealed package 44. All that would be needed then is to attach the lid 54.

The entire non-toxic biocompatible RFID tag 40 of FIGS. 9-11 could be molded or embedded in a thin medical grade plastic disk. This could be a thin silicone disk, a thin epoxy disk or a thin polyimide disk. With a suitable adhesive, this would allow it to be attached to, for example, the housing or header block of the AIMD 10. It could also be implanted through a small incision in various other locations in the body, or it could even be injected with a large needle syringe (if properly configured).

The novel biocompatible antenna 42 and hermetically sealed RFID chip 50 of the present invention does not need to be associated with a pacemaker or other type of AIMD 10. The RFID chip 50 and associated biocompatible and non-toxic antenna 42 could be implanted in the abdominal area, into the arm or even the buttocks. Since these areas are all subject to some movement, flexibility of the antenna 42 is important. The antenna 42 and hermetically sealed RFID chip 50 could be over-molded with silicone or other thin biocompatible but flexible material. Flexibility of the entire structure is important because no matter where you implant this in the human body, it is subject to some motion. The arm would be an extreme example where motion could occur. The novel RFID tag 40 need not be for identification of a medical implant only. It could also be used generally for human identification. This would include applications where lights in a building could be turned on and off automatically as the implanted RFID tag 40 is sensed, doors could be opened and the like. The RFID chip 50 could also contain encrypted information such as Social Security Number, credit card information and the like. This would facilitate automated checkout from retail stores and the like.

Figure 12:
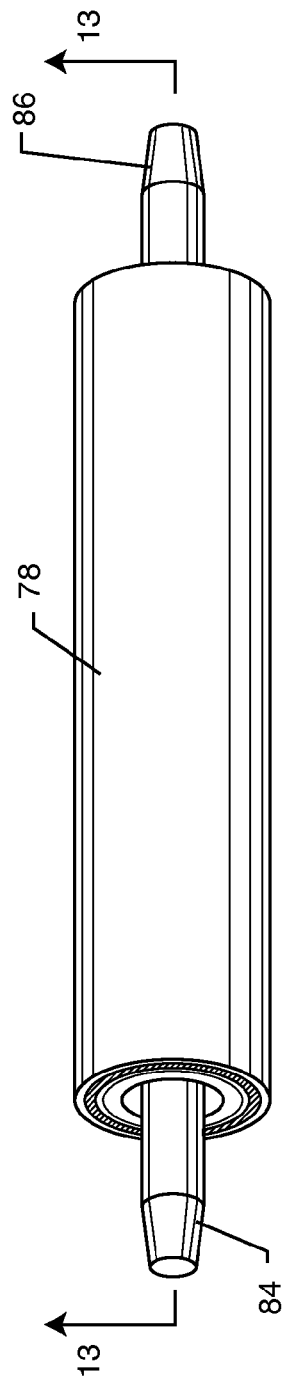
FIG. 12 is a perspective view of an alternative cylindrical hermetic seal utilized to house the RFID microchip.

FIG. 12 illustrates an alternative cylindrical hermetically sealed package 78 to house the RFID microchip 50 which is very similar to the package 44 shown in FIGS. 9-11.

Figure 13:
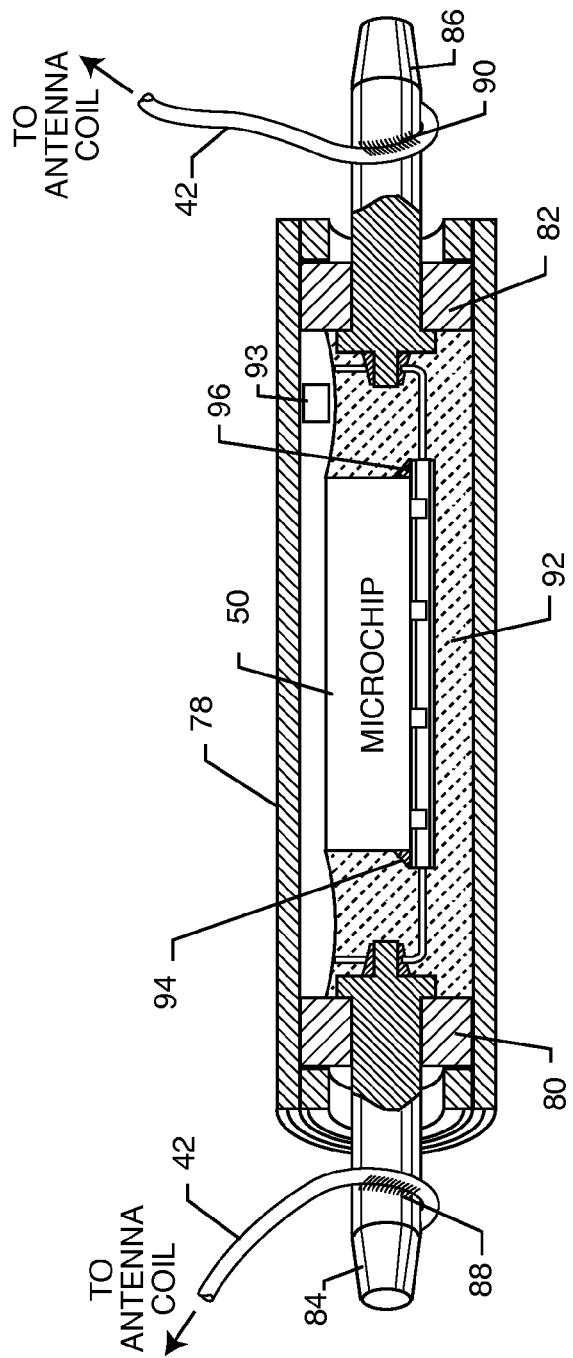
FIG. 13 is a sectional view taken generally along the line 13-13 from FIG. 12.

FIG. 13 is a sectional view taken along line 13-13 from FIG. 12. Shown is an RFID microchip 50 within the hermetic package 78. On either end are hermetic seals 80 and 82, and two pins 84 and 86 extending therethrough. These pins 84 and 86 are electrically isolated from the overall hermetic package 78. It is important that all of the surfaces that could possibly be exposed to body fluids be both non-toxic and biocompatible. In a preferred embodiment, the housing 78 would be of either titanium or platinum. The pins 84 and 86 could also be platinum or similar noble material. The hermetic seals 80 and 82 may be gold brazed alumina seals as are commonly used in AIMDs, or they may include compression or fusion glass seals. Electrical connections 88 and 90 are formed between the ends of the antenna coil 42 and both pins 84 and 86. The electrical connections 88 and 90 may be formed by laser welding or suitable biocompatible thermal-setting conductive adhesives, gold brazes or the like.

FIG. 13 shows the microchip 50 embedded in an optional encapsulant 92. This can be any type of non-conductive epoxy, silicone or the like. Since it's inside the hermetic seal, it is not important that the encapsulating 92 be non-toxic or biocompatible. The purpose of the encapsulating 92 is to simply provide mechanical stability for the microchip 50 so that it is resistant to shock and vibration or movement within the human body. There is also an optional desiccant 93 within the package 78. There are electrical connections 94 and 96 which are typically solder joints which connect the RFID chip 50 to pins 84 and 86. There are also a number of other connections on the microchip 50 itself. If one were to look at a high magnification photograph of a microchip 50, one would see that there are literally hundreds or even thousands of miniature electrical connections. The materials in the electrical connections of the microchip 50 itself are generally not biocompatible and can be toxic to body tissue. This is another important reason why both the microchip 50 and all of its associated electrical components and connections must be housed inside a non-toxic hermetically sealed biocompatible package, housing or container. When attached to the multi-turn RFID loop antenna 42, the entire structure consisting of fine wire is relatively flexible.

Figure 14:
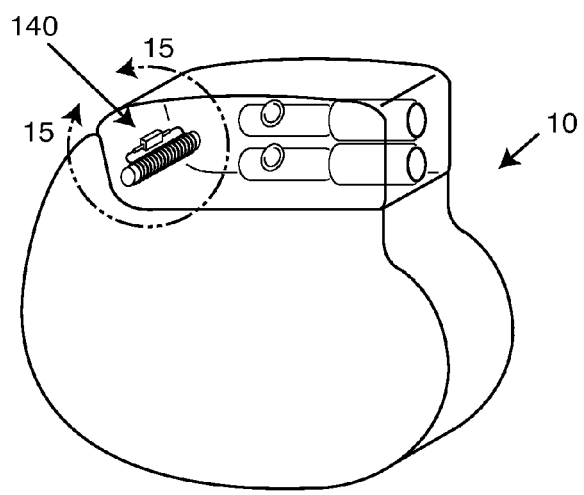
FIG. 14 is a perspective view of an AIMD having an RFID tag embodying the present invention embedded in a header block thereof.

FIG. 14 illustrates a prior art AIMD 10, such as a cardiac pacemaker similar to that shown in FIG. 9, except that it includes another type of an RFID tag 140 which embodies the present invention. The RFID tag 140 includes a hermetically sealed RFID chip 144 and a biocompatible antenna 142. The biocompatible antenna 142 is a solenoid-type antenna which may be optionally wound around a ferrite core 146. Solenoid type RFID antennas are well known in the art. See, for example, U.S. Pat. No. 7,443,362, the contents of which are incorporated herein by reference.

Figure 15:
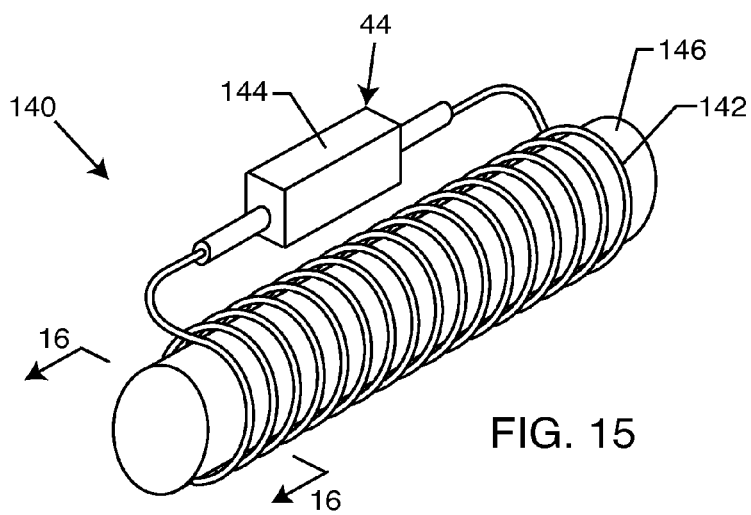
FIG. 15 is an enlarged perspective view of an RFID tag structure embodying the present invention and taken generally of the area designated by line 15-15 of FIG. 14.

FIG. 15 is an enlarged view taken generally along line 15-15 from FIG. 14. The hermetically sealed RFID microelectronic chip 144 comprises the same package 44 that was illustrated in FIG. 11. Also, shown is the biocompatible antenna 142 which consists of multiple turns of biocompatible wire in a solenoid-type configuration wound about an optional ferrite core 146, which has an optional biocompatible coating 148.

Figure 16:
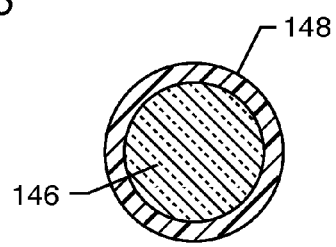
FIG. 16 is a cross-sectional view taken generally along line 16-16 of FIG. 15.

FIG. 16 is a sectional view of the ferrite core 146 taken generally along line 16-16 from FIG. 15. The ferrite core 146 consists of a high temperature sintered ferrite material. This is important because it reaches a ceramic-type state wherein the magnetic dipoles are tightly bound up within the ceramic matrix, which is important for biocompatibility so that toxic ferromagnetic materials, such as nickel alloys, do not leach out. The optional biocompatible conformal coating 148 consists of a dielectric material which can include parylene, ETFE, PTFE, polyimide, polyurethane, silicone or the like.

Referring to FIGS. 14-16, it is important in implant applications for humans that the ferrite material of the core 146 be carefully chosen. This has to do with the fact that the human may at some point in his or her life, undergo a medical diagnostic procedure known as magnetic resonance imaging (MRI). MRI equipment embodies three main fields, one of which is known as the $B_0$ main static field. The main static field of an MRI scanner is more than a hundred thousand times more powerful that the earth's magnetic field. This tends to align magnetic domains of a ferromagnetic material. Since it is not important that the RFID tag be read during an actual MRI scan, then it is not particularly important that the ferrite material be saturated during an MRI scan. In the saturated condition, the antenna 142 would become highly inefficient. What this means is it would not be possible to interrogate the RFID tag 140 while the patient was in the presence of a main static field of an MRI scanner. However, this would require that the patient be inside the bore of the MRI scanner at which time there is really no need that the RFID tag 140 be operable. What is important in the present invention is that the magnetic ferrite material that is used be carefully selected such that it not be permanently damaged by exposure to the main static field. Certain ferrite materials, when exposed to a powerful magnetic field, will have their magnetic dipoles aligned. After removal of the powerful magnetic field, those dipoles will remain aligned in a condition known as magnetic remanence. This is a form of magnetic memory which would be very detrimental. If the ferrite material remained in a remanent condition, this would mean that the RFID tag 140 would be ruined and would no longer be capable of being read after the MRI scan. Accordingly, it is a feature of the present invention that the selection of the ferrite be done generally using soft ferrites or other ferrite material that will not exhibit permanent remanence after exposure to MRI.

Figure 17:
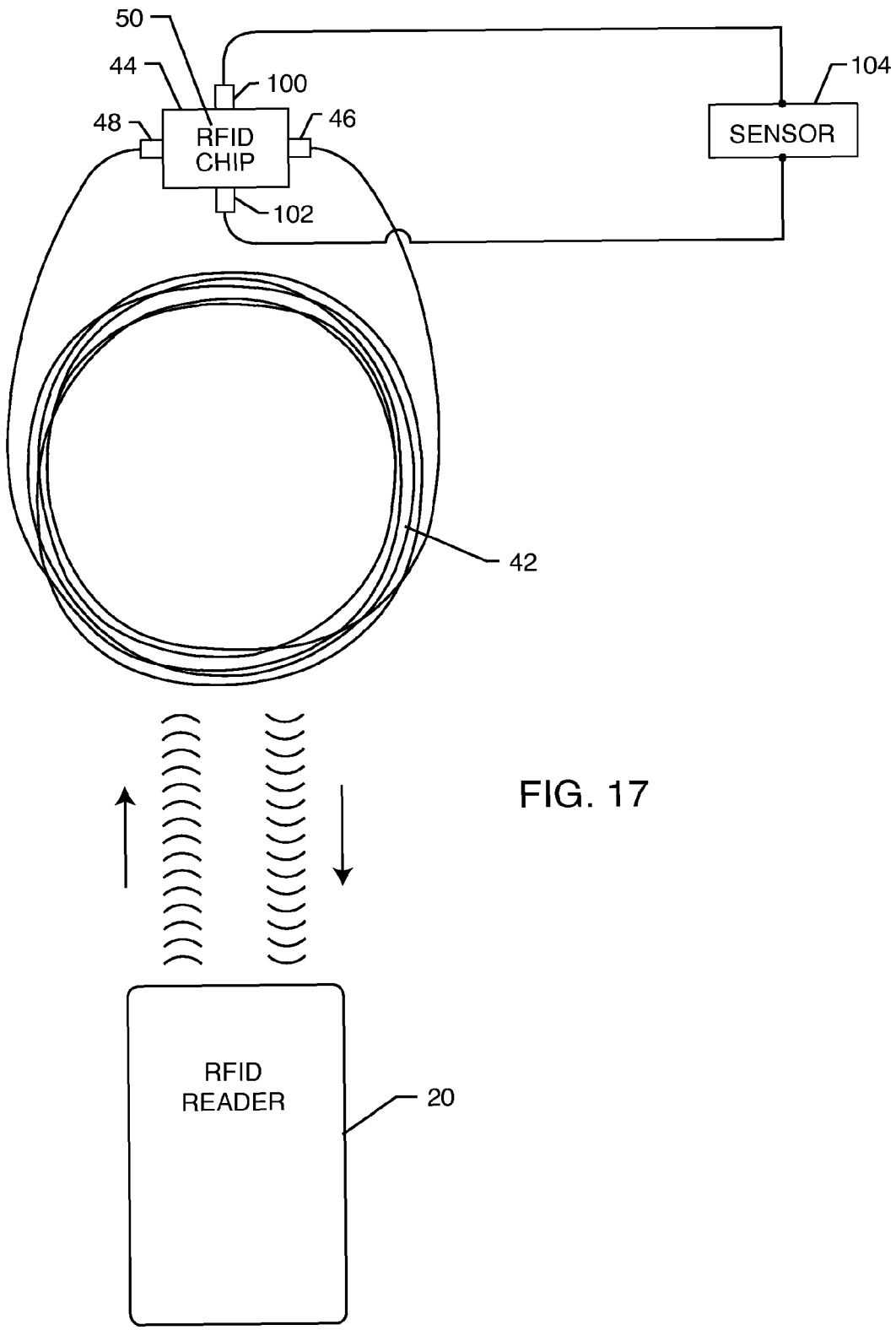
FIG. 17 is a block diagram illustrating a system of an RFID reader communicating with a hermetically sealed RFID chip which is associated with a biocompatible antenna.

FIG. 17 is a block diagram showing an RFID reader 20 that is communicating with a hermetically sealed RFID chip 50 associated with a biocompatible antenna 42 of the present invention. The RFID chip 50 is enclosed within a hermetic package 44 similar to that shown in FIG. 11, except that it has four terminals instead of two. The other two terminals 100 and 102 are connected to an external sensor 104. The sensor 104 can be any of a variety of sensors which transmit important information about activities within the human body. For example, this could be an accelerometer, a pressure transducer, for example, to measure pressures within a cardiac chamber, a motion sensor to measure cardiac ventricular wall motion, blood gas sensors and the like. When interrogated, the RFID chip 50 would take information from the sensor 104 and transmit it to the RFID reader 20. In this way, medical personnel could, in real time, gain important information about the patient. For example, if the patient had a heart valve replacement, the RFID chip 50 and sensor 104 could be associated with said valve. The RFID chip 50 could transmit important information about the proper operation of the prosthetic heart valve leaflets.

Figure 18:
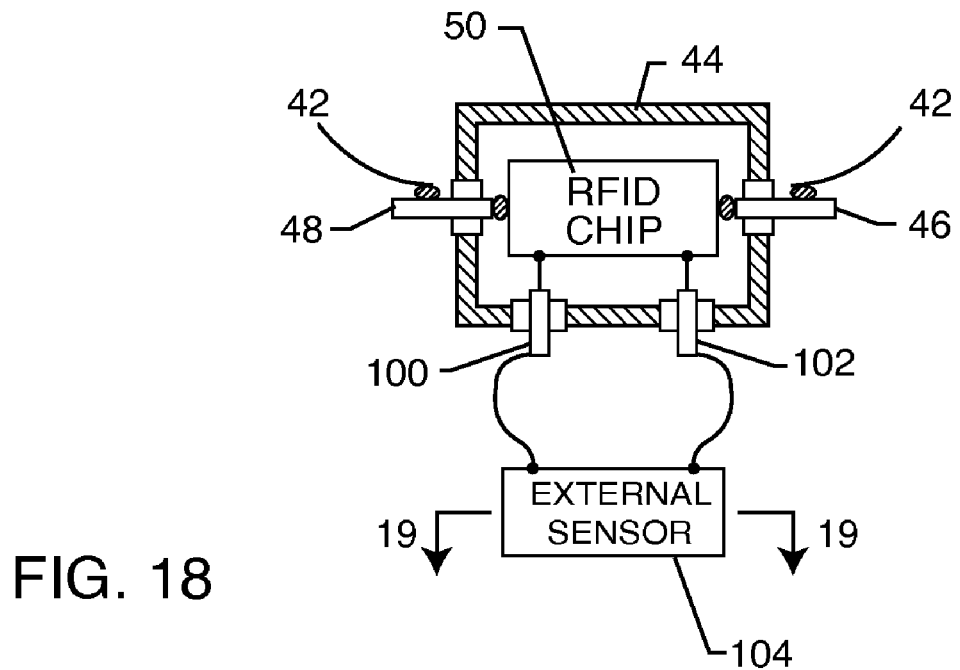
FIG. 18 illustrates the RFID chip in its own hermetic package and wired to an external sensor.

FIG. 18 is very similar to FIG. 17 with the RFID chip 50 in its own hermetic package 44 and wired through terminal pins 46 and 48 to an external biocompatible antenna 42. An external sensor 104 is wired to the RFID chip 50 through terminal pins 100 and 102.

Figure 19:
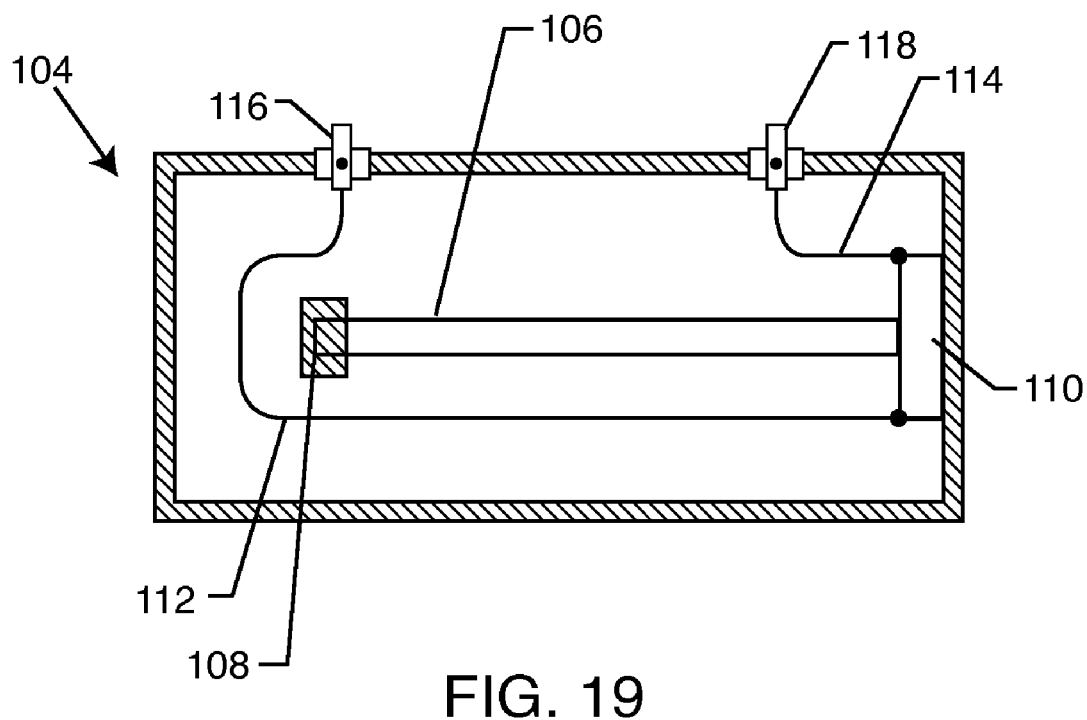
FIG. 19 is a sectional view of the external sensor shown in FIG. 18.

FIG. 19 is a sectional view taken along line 19-19 of FIG. 18. In this case, the sensor 104 is a motion sensor that includes a piezoelectric cantilever arm 106 with a weight 108 attached to its end. With motion, the cantilever arm 106 deflects or oscillates and generates electricity through piezoelectric action. The cantilever arm 106 is connected to a base 110 and lead wires 112 and 114 are routed to terminal pins 116 and 118.

Figure 20:
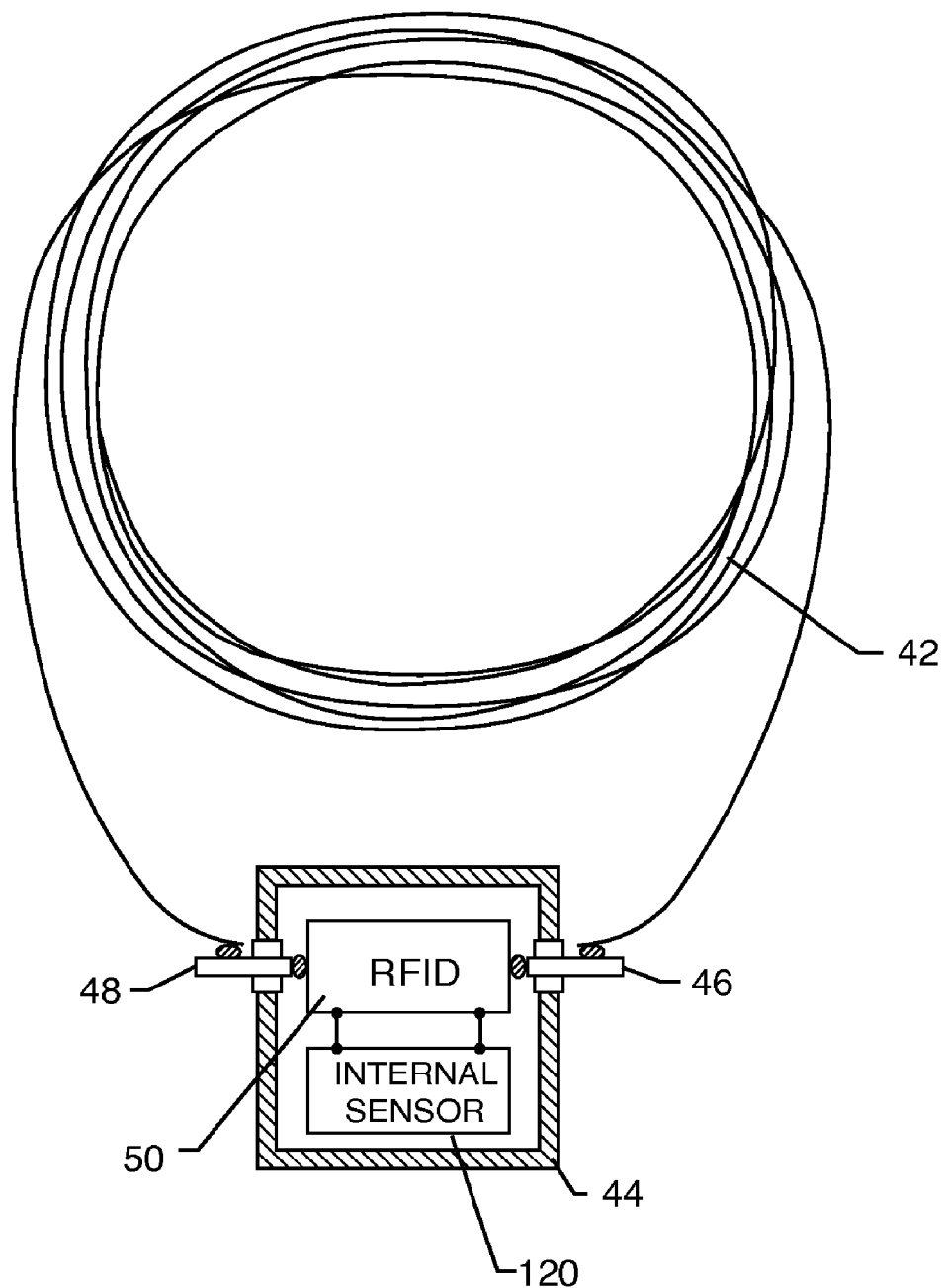
FIG. 20 is a view similar to FIG. 18, with the exception that the RFID chip is connected to an internal sensor.

FIG. 20 is similar to FIGS. 17-19 except that the RFID chip 50 is connected to an internal sensor 120. The hermetic housing 44 is shown for convenience and, of course, can be the overall hermetically sealed housing of the AIMD itself.

Figure 21:
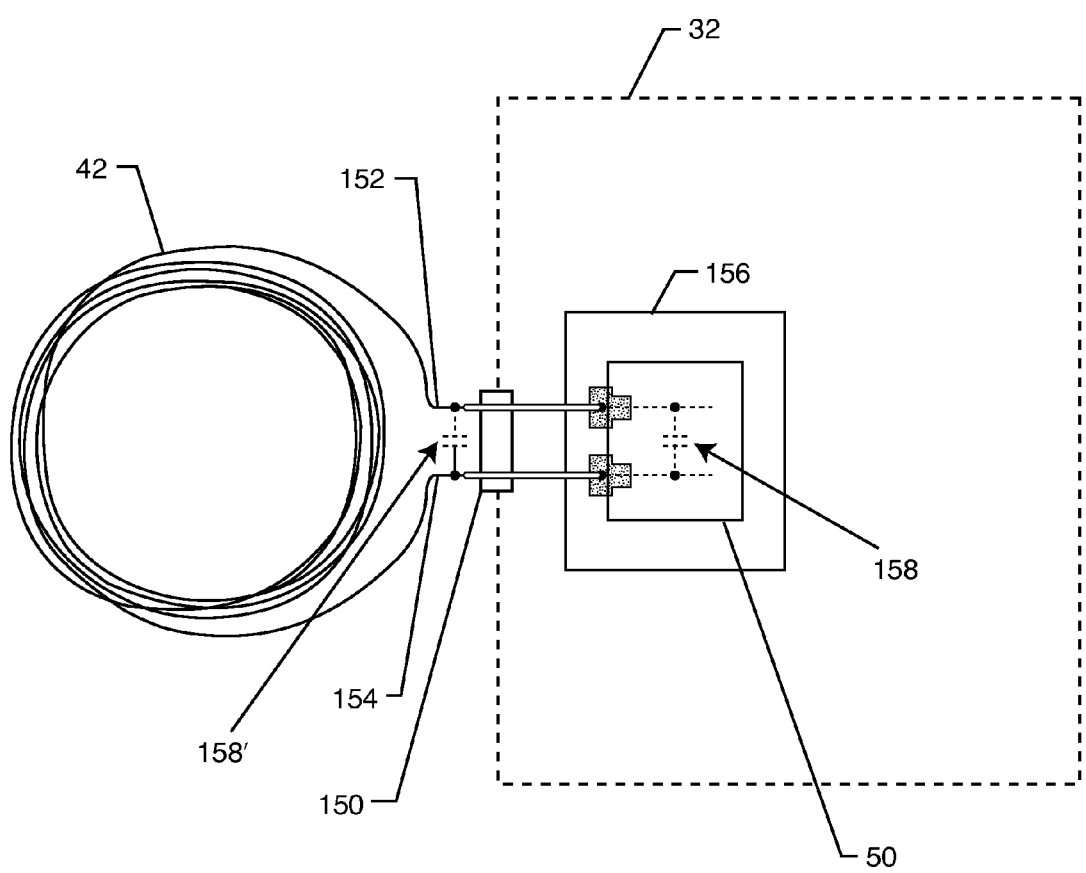
FIG. 21 is similar to FIG. 20, except that the biocompatible antenna is disposed on the outside of the AIMD housing.

FIG. 21 illustrates a biocompatible antenna 42 of the present invention which is disposed on the outside of an AIMD housing 32. Shown is a bipolar hermetic terminal 150 through which the antenna leads 152 and 154 pass through in non-conductive relation. The hermetic terminal 150 forms a continuous part of the hermetic housing 32 of the AIMD. The antenna leads 152 and 154 are connected to a circuit board 156 on which is disposed the microelectronic RFID chip 50. Contained within or adjacent to the RFID chip 50 is a capacitor 158. The capacitor 158 is generally wired in parallel with the RFID chip 50 and the antenna 42. The purpose of the capacitor 158 is to resonate with the external antenna 42 such that an optimal amount of energy is captured from an external RFID reader (not shown). The capacitor 158 stores energy which powers the passive RFID chip 50. The energy stored in the capacitor 158 provides enough energy for the RFID chip 50 to transfer its stored information back to an external RFID reader. The RFID chip 50 as previously described was a passive RFID chip. This means that it does not have its own internal power source or battery and gathers all its energy from an external reader 20. However, the present invention is not limited to just passive RFID chips. Active RFID chips may also be employed. An active RFID chip would get its energy from the AIMD power source (battery) and would therefore be more powerful.

The structure illustrated in FIG. 21 has a number of very important advantages. First, the antenna 42 is disposed on the outside of the hermetically shielded and hermetic housing 32 of the AIMD. This means that the antenna 42 will not be shielded by the AIMD housing 32 so that it can more effectively capture energy and communicate with an external reader. By disposing the microelectronic RFID chip 50 and its associated capacitor 158 on the inside of the AIMD housing 32, the need to hermetically seal it or construct the RFID chip 50 from biocompatible materials is eliminated. The RFID chip 50 is disposed within the overall hermetically sealed housing 32 of the AIMD and is therefore never exposed to body fluids. Accordingly, the need for a separate hermetically sealed package 44 as shown in FIGS. 10 and 11 is no longer needed. This approach offers a number of very important advantages, including ease of construction and cost reductions. The capacitor 158 may also be disposed on the outside or body fluid side of the hermetic terminal 150. An advantage of this placement is that a higher Q resonance could be obtained between the capacitor 158' and the antenna structure 42. If the capacitor 158' was placed on the outside of the AIMD hermetic housing 32, it would be directly exposed to body fluids. Methods of construction for capacitors directly exposed to body fluid are disclosed in U.S. Pat. No. 7,535,693, the contents of which are incorporated herein.

Figure 22:
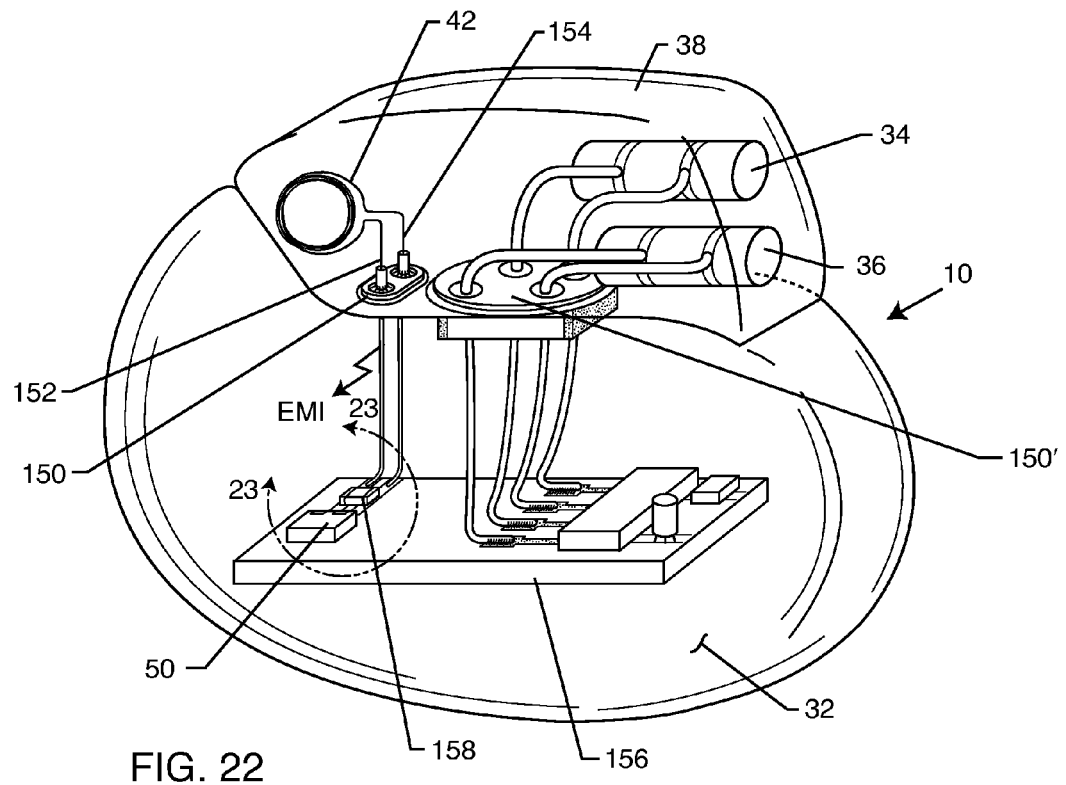
FIG. 22 is a perspective view of a cardiac pacemaker embodying the configuration of the RFID tag illustrated in FIG. 21.

FIG. 22 is an isometric view of a cardiac pacemaker 10 embodying the features previously described in connection with FIG. 21. Shown is the RFID antenna 42 which is desirably cast in the plastic or Techothane header block 38 of the pacemaker 10. Leadwires 152 and 154 are connected to RFID chip 50 which is also in parallel with its resonant capacitor 158.

Figure 23:
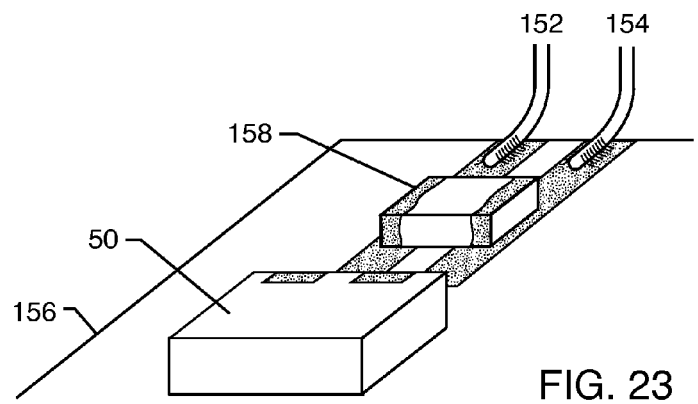
FIG. 23 is an enlarged sectional view taken of the area indicated by line 23-23 from FIG. 22, illustrating the microelectronic RFID chip connected to its resonant capacitor and routed to leadwires which extend to the biocompatible antenna.

FIG. 23 is taken generally of the area designated by line 23-23 of FIG. 22, and shows in close-up view the microelectronic RFID chip 50 which is connected to its optional resonant capacitor 158 and then routed to leadwires 152 and 154. Also shown is a quad polar hermetic terminal 150' though which the pacing and sensing leadwires pass in non-conductive relation to internal circuits. These quad polar leads are connected through IS-1 connectors 34 and 36 as shown.

Figure 24:
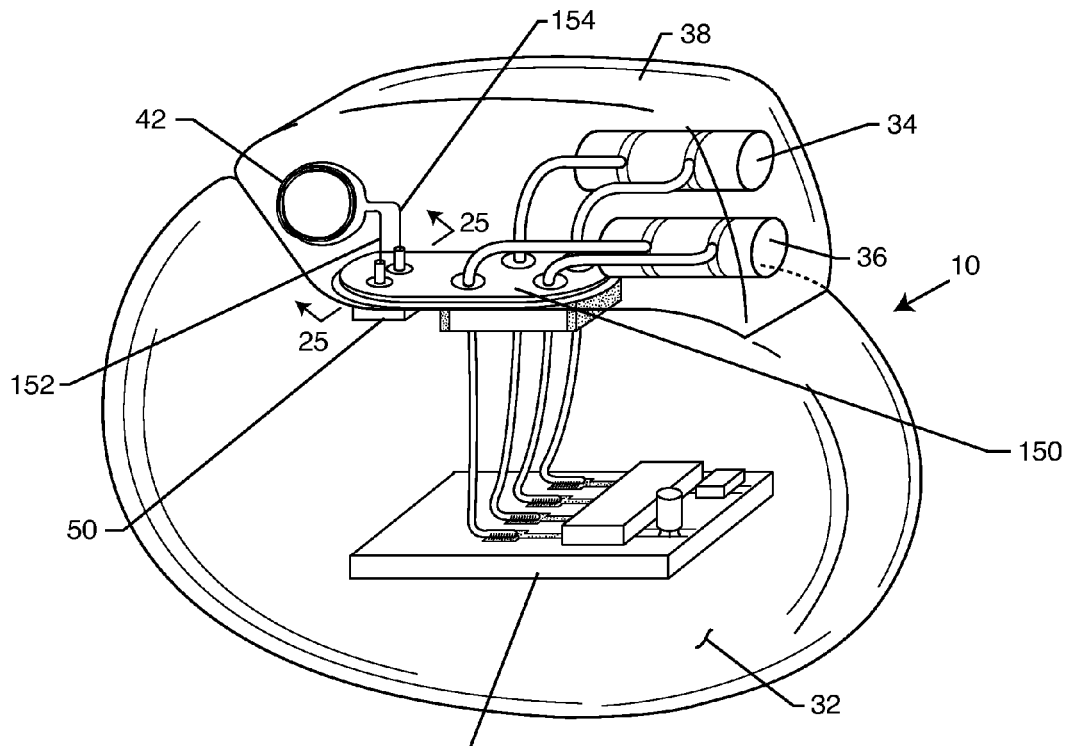
FIG. 24 is a view similar to FIG. 22, except that the RFID chip is either mounted very close or directly adjacent to the hermetic terminals for the antenna leadwires.

FIG. 24 is similar to FIG. 22 except that the RFID chip 50 is either mounted very close or directly adjacent to or on the hermetic terminal 150". This offers a number of important advantages. By having the RFID chip 50 very close to the point of leadwire 152 and 154 ingress and egress through the hermetic terminal 150, one can preserve the quality factor (Q) of the circuit that is formed between capacitor 158 and external antenna 42. In addition, by keeping leadwires 152 and 154 very short as they enter the AIMD housing 32, one also eliminates the possibility that electromagnetic interference (EMI) from other sources could gain entry into the inside of the AIMD housing and undesirably couple to sensitive AIMD circuits. For example, a closely held cellular telephone may induce undesirable EMI onto the antenna structure 42. It would be undesirable to have this EMI re-radiate inside of the AIMD housing 32 as illustrated as EMI in FIG. 22. The hermetic terminal 150" of FIG. 24 does differ from the one shown in FIG. 22. In FIG. 22, there are actually two hermetic terminals. One is the bipolar hermetic terminal 150 to connect to the external RFID antenna 42. The second is a quad polar hermetic terminal 150' which is connected to IS-1 connectors 34 and 36. In FIG. 24, these two hermetic terminals have been integrated into one single hex-polar hermetic terminal 150" which supports both functions.

Figure 25:
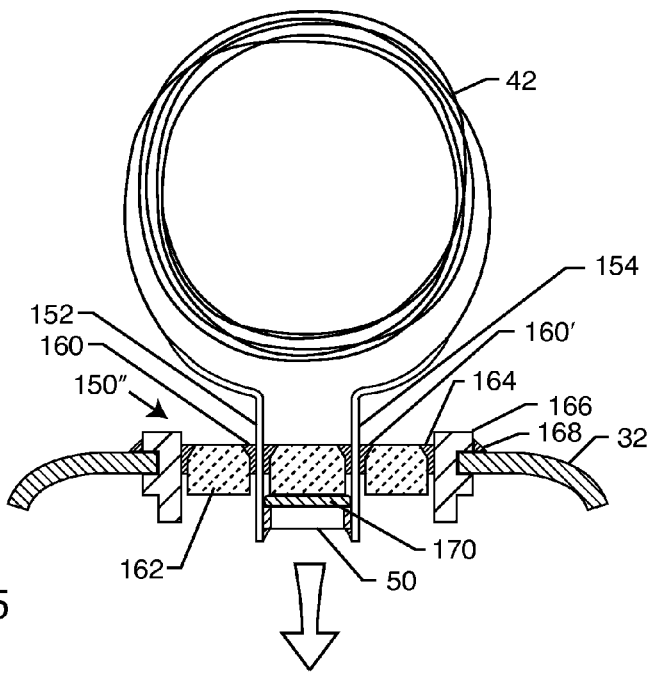
FIG. 25 is an enlarged, fragmented sectional view taken generally along the line 25-25 from FIG. 24.

FIG. 25 is a cross-sectional view taken generally along line section 25-25 from FIG. 24. Shown is the biocompatible antenna structure 42 which is disposed on the outside or body fluid side of AIMD housing 32. Also shown in cross-section is the hermetic terminal 150". In this case, leads 152 and 154 are a continuous part of the antenna structure 42. The antenna wires 152 and 154 are routed in non-conductive relation through the hermetic terminals 150". They are then gold brazed 160 and 160' to the insulator structure 162 of the hermetic terminal 150". Hermetic terminals are well known in the prior art and can consist of gold brazed hermetic terminals with alumina insulators; or compression or fused glass, and the like. There is also another gold braze 164 which hermetically seals the insulator 162 to ferrule 166. The ferrule 166 is generally of titanium or similar biocompatible material. The housing of the AIMD 32 is generally laser welded 168 to the ferrule 166 of the hermetic terminal 150". In this case, the RFID chip 50 is shown bonded through an insulating adhesive 170 directly to one surface of the hermetic terminal 150. It is not necessary that the RFID chip 50 be directly bonded to the hermetic terminal 150, but it is desirable, as previously mentioned, that it at least be in close proximity. In a preferred embodiment, the RFID chip 50 is installed immediately adjacent to the hermetic terminal 150.

Figure 26:
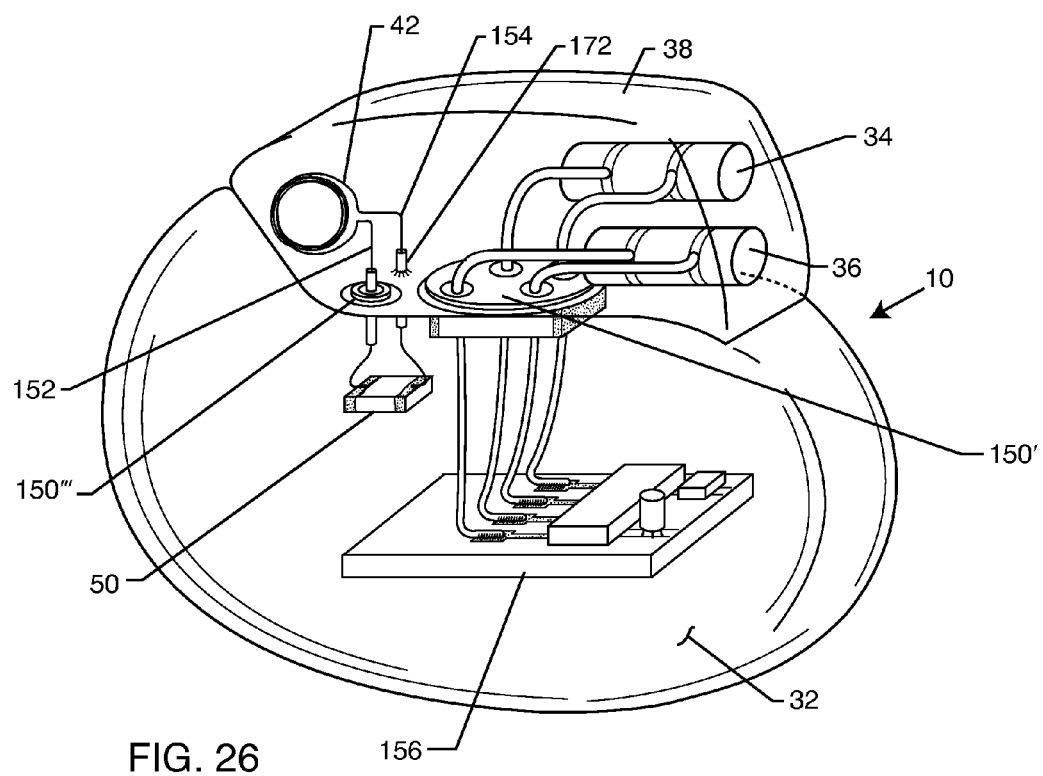
FIG. 26 is similar to FIGS. 22 and 24, except that a unipolar hermetic terminal is provided.
Figure 27:
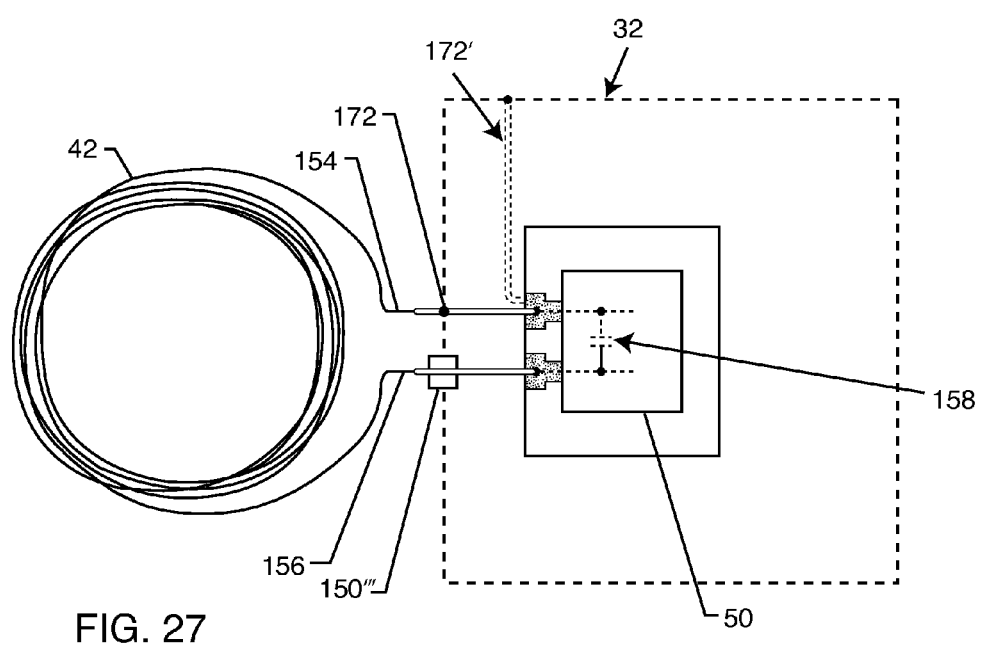
FIG. 27 is a schematic illustration similar to FIG. 21, illustrating the configuration of the RFID tag in relation to the AIMD housing and the hermetic terminal of FIG. 26.

FIGS. 26 and 27 show an alternative embodiment to those shown in FIGS. 22 and 24. Here, a unipolar hermetic terminal 150''' is incorporated. Every pin that is routed through a hermetic terminal adds to its cost. This is because of the cost associated with the terminal pin and the additional need for sputtering of the insulator, additional gold brazed rings and the like. Accordingly, substantial cost can be saved if one reduces the number of terminal pins that are routed through a hermetic seal. In FIG. 26, there is a single unipolar hermetic terminal 150''' which is adjacent to a pin 172 which is laser welded directly to the housing 32 of the AIMD 10. Laser welding a pin 172 through a hole in the titanium can 32 is a relatively simple and cost effective procedure. Antenna lead 152 is shown connected to the unipolar pin of the hermetic terminal 150'''. The other antenna lead 154 is shown connected to the grounded pin 172 which is electrically connected to the overall housing 32 of the AIMD 10. The RFID chip 50 is connected to the unipolar pin or antenna lead 172 and also to the other side of the ground pin 122. In fact, the ground side of the RFID chip 50 could be connected anywhere inside of the AIMD (alternate ground 177'-FIG. 27) as long as it was connected to ground associated with the AIMD housing 32. In other words, it need not be connected directly to the same terminal pin as ground extends everywhere the AIMD housing 32 extends.

From the foregoing it will be appreciated that a novel aspect of the present invention resides in providing a relatively large non-hermetically sealed biocompatible multi-turn RFID loop antenna 42 which is electrically connected to a miniature RFID chip 50 that is enclosed within its own hermetically sealed miniature package 44. The hermetic package 44 can be very small and the loop antenna 42 can be relatively large wherein the entire RFID tag 40 is both highly reliable, resistant to body fluids and completely biocompatible. In a particularly preferred embodiment, the hermetic seal for the RFID chip 50 is the overall shielded metallic housing 32 of the AIMD 10. The external antenna structure 42 is adaptable for being molded into the header block 38, for example, for a cardiac pacemaker 10 or, alternatively it can be implanted in other locations in the human body.

The hermetically sealed RFID chip with fixation device can be used to attach to one or more abandoned leads in the pectoral pocket. This is very useful whether or not the patient receives a new pacemaker or AIMD, implant or not. That is, if a patient that has reverted to normal sinus rhythm and no longer needs a pacemaker and has abandoned leads, the radiology department can quickly tell through the RFID scan whether or not abandoned lead wires are present. As mentioned, this is extremely important to prevent inadvertent MRI on such a patient. In the past, it has been shown that abandoned leads can heat up so much that ablation of cardiac tissue and even perforation of cardiac walls can occur. It is, therefore, a feature of the present invention that both the lead wire system and the AIMD can be separately identified.

It will also be appreciated that the present invention provides an improved implantable radio frequency identification (RFID) tag that may be used advantageously with an active implantable medical device (AIMD) wherein the RFID microelectronics chip is disposed within the AIMD housing and the biocompatible antenna extends from the RFID microelectronics chip exteriorly of the housing, for example, into the non-hermetically sealed header block for the AIMD. At least one of the leads connecting the antenna to the RFID chip will normally extend through the hermetic terminal associated with the AIMD housing. The RFID chip may be disposed adjacent to the hermetic terminal, or be remotely disposed within the housing relative to the hermetic terminal. The present invention advantageously utilizes the hermetically sealed housing for the AIMD as a hermetically sealed biocompatible container to prevent the RFID microelectronics chip from coming into contact with body fluids or tissue.

Although several embodiments have been described in detail for purposes of illustration, various modifications may be made without departing from the scope and spirit of the invention. Accordingly, the invention is not to be limited, except as by the appended claims.

What is claimed is:

1. An implantable medical device, comprising:
   a) a hermetically sealed biocompatible housing;
   b) an RFID microelectronics chip disposed within the housing;
   c) an antenna wire having a first end portion electrically connected to a first end of the RFID chip inside the housing and extending along a length to a second end portion electronically connected to a second end of the RFID chip inside the housing with at least an intermediate portion of the length of the antenna wire between the first and second end portions residing outside the housing; and
   d) a sealing material that hermetically seals against an outer surface of the first and second end portions of the antenna wire and against respective perimeter openings in the housing through which the antenna wire extends, wherein the intermediate portion of the antenna wire external to the housing serves as an antenna for the RFID microelectronics chip.

2. The implantable medical device of claim 1 wherein the housing has a helium leak rate of no more than $10^{-7}$ cubic centimeters per second.

3. The implantable medical device of claim 2 wherein the housing is of a material selected from the group consisting of biocompatible metals and alloys, ceramic, glass, porcelain, sapphire and composites thereof, and specialty polymer composites.

4. The implantable medical device of claim 3 including a desiccant within the housing.

5. The implantable medical device of claim 3 including an encapsulant within the housing surrounding at least a portion of the RFID chip.

6. The implantable medical device of claim 5 wherein the encapsulant is comprised of a thermal-setting polymer or a silicone material.

7. The implantable medical device of claim 1 wherein the housing includes a cap hermetically sealed to an open end of a housing container.

8. The implantable medical device of claim 1 wherein the RFID chip is read-only or readable/writable.

9. The implantable medical device of claim 1 wherein the RFID chip is communicable with an external device at a radio frequency of from 125 kHz to 915 MHz.

10. The implantable medical device of claim 9 wherein the RFID chip is communicable with an external device at a radio frequency of approximately 13.56 MHz.

11. The implantable medical device of claim 1 wherein the RFID chip includes information relating to a patient in which the medical device is implanted.

12. The implantable medical device of claim 1 wherein the container, RFID chip, and at least the first and second end portions of the antenna wire are embedded within a non-conductive biocompatible material.

13. The implantable medical device of claim 12 wherein the biocompatible material comprises a disc of a material selected from the group consisting of silicone, epoxy, and a medical grade plastic.

14. The implantable medical device of claim 1 wherein the intermediate portion, of the antenna wire is wound around a ferrite-based core.

15. The implantable medical device of claim 14 wherein the ferrite-based core comprises a high temperature sintered ferrite-based material.

16. The implantable medical device of claim 15 including a biocompatible dielectric material at least partially coating the ferrite-based material.

17. The implantable medical device of claim 16 wherein the biocompatible dielectric material is selected from the group consisting of parylene, ETFE, PTFE, polyimide, polyurethane, and silicone.

18. The implantable medical device of claim 14 wherein the ferrite-based core is comprised of a ferrite material that will not exhibit permanent remanence after exposure to MRI fields.

19. The implantable medical device of claim 1 including a sensor conductively coupled to the RFID microelectronics chip.

20. The implantable medical device of claim 19 wherein the sensor is disposed exterior of the hermetically sealed housing.

21. The implantable medical device of claim 19 wherein the sensor is disposed within the hermetically sealed housing.

22. The implantable medical device of claim 19 wherein the RFID chip is capable of transmitting data measured by the sensor in real time.

23. The implantable medical device of claim 2 wherein the measurable data comprises the activity of a human body.

24. The implantable medical device of claim 1 wherein the intermediate portion of the antenna wire is a multi-turn antenna.

25. The implantable medical device of claim 1 wherein the first and second end portions of the antenna wire are first and second feedthrough wires that are hermetically sealed in the respective openings in the housing and opposed end of the intermediate portion of the antenna wire are electrically connected to the first and second feedthrough wires.

26. The implantable medical device of claim 1 wherein the hermetically sealed housing is the housing for the active implantable medical device.

27. The implantable medical device of claim 1 wherein the hermetically sealed housing s of titanium or stainless steel.

28. An implantable medical device, comprising:
   a) a hermetically sealed biocompatible housing;
   b) an RFID microelectronics chip disposed within the housing;
   c) an antenna wire having a first end portion electrically connected to a first end of the RFID chip inside the housing and extending along a length to a second end portion electronically connected to a second end of the RFID chip inside the housing with at least an intermediate portion of the length of the antenna wire between the first and second end portions residing outside the housing; and
   d) wherein a wall of the housing hermetically seals against an outer surface of the first and second end portions of the antenna wire, wherein the intermediate portion, of the antenna wire external to the housing serves as an antenna for the RFID microelectronics chip.

29. The implantable medical device of claim 28 wherein the housing has a helium leak rate of no more than $10^{-7}$ cubic centimeters per second.

30. An implantable medical device, comprising:
   a) a hermetically sealed biocompatible housing;

b) an RFID microelectronics chip disposed within the housing;
c) a first feedthrough, wire comprising a first proximal end electrically connected to the RFID chip and a first distal end residing outside the hermetically sealed housing, wherein a first sealing material hermetically seals against an outer surface of the first feedthrough wire and against a first perimeter opening in the housing through which the first feedthrough wire extends;
d) a second feedthrough wire comprising a second proximal end electrically connected to the RFID chip and a second distal end residing outside the hermetically sealed housing, wherein a second sealing material hermetically seals against an outer surface of the second feedthrough wire and against a second perimeter opening in the housing through which the second feedthrough wire extends; and
e) an antenna wire having a first end electrically connected to the first distal end of the first feedthrough wire outside the housing and extending along a length to a second end electronically connected to the second distal end of the second feedthrough wire outside the housing.

31. The implantable medical device of claim 30 wherein the housing has a helium leak rate of no more than $10^{-7}$ cubic centimeters per second.

32. A medical system comprising:
a) an implantable medical device;
b) hermetically sealed biocompatible housing that is either contained inside the implantable medical device or contacted, to an outer surface thereof;
c) an RFID microelectronics chip disposed within the housing;
d) an antenna wire having a first end portion electrically connected to a first end of the RFID chip inside the housing and extending along a length to a second end portion electronically connected to a second end of the RFID chip inside the housing with at least an intermediate portion of the length of the antenna wire between the first and second end portions residing outside the housing; and
e) a sealing material that hermetically seals against an outer surface of the first and second end portions of the antenna wire and against respective perimeter openings in the housing through which the antenna wire extends, wherein the intermediate portion of the antenna wire external to the housing serves as an antenna for the RFID microelectronics chip.

33. The system of claim 32 wherein the housing has a helium leak rate of no more than $10^{-7}$ cubic centimeters per second.

34. The system of claim 32 including an interrogator for electromagnetically communicating with the RFID chip.

35. The system of claim 33 wherein the interrogator is a read only or a reader/writer device.

36. The system of claim 33 wherein the interrogator is capable of communicating with a computer or a computer network.

37. The system of claim 32 wherein the hermetically sealed housing for the RFID chip is disposed within a non-hermetically sealed portion of the medical device.

38. The system of claim 32 wherein the hermetically sealed housing for the RFID chip is disposed within a header block of the medical device.

39. The system of claim 32 wherein the antenna wire and the RFID chip are disposed within the medical device parallel to a length and height plane of the medical device, and midway through the width thereof.

40. The system of claim 32 wherein the RFID chip includes information pertaining to the medical device.

41. The system of claim 32 wherein the implantable medical device is selected from the group consisting of a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion or a prosthetic device, and component parts thereof, including lead wires and abandoned lead wire.

* * * * *